US010507318B2

(12) United States Patent
Jin et al.

(10) Patent No.: US 10,507,318 B2
(45) Date of Patent: Dec. 17, 2019

(54) SELF-CLOSING BAG CONNECTOR

(71) Applicant: ConvaTec Technologies Inc., Las Vegas, NV (US)

(72) Inventors: Yun Jin, Bedminster, NJ (US); Bret Alexander Weig, Browns Mills, NJ (US); John Cline, New Brunswick, NJ (US); Mingliang Lawrence Tsai, Holmdel, NJ (US)

(73) Assignee: ConvaTec Technologies Inc., Las Vegas, NV (US)

( * ) Notice: Subject to any disclaimer, the term of this patent is extended or adjusted under 35 U.S.C. 154(b) by 0 days.

(21) Appl. No.: 15/495,712

(22) Filed: Apr. 24, 2017

(65) Prior Publication Data

US 2017/0252549 A1 Sep. 7, 2017

Related U.S. Application Data

(63) Continuation of application No. 14/449,035, filed on Jul. 31, 2014, now Pat. No. 9,669,205.

(Continued)

(51) Int. Cl.
*F16L 37/32* (2006.01)
*A61M 39/10* (2006.01)
(Continued)

(52) U.S. Cl.
CPC ........... *A61M 39/10* (2013.01); *A61F 5/4405* (2013.01); *A61M 39/1011* (2013.01);
(Continued)

(58) Field of Classification Search
CPC . F16L 37/30; F16L 37/32; F16L 37/34; F16L 37/367; F16L 37/38; A61M 39/10
See application file for complete search history.

(56) References Cited

U.S. PATENT DOCUMENTS 851,530 A 4/1907 Lamport
2,254,997 A 9/1941 Fisher
(Continued)

FOREIGN PATENT DOCUMENTS

CN 105407961 A 3/2016
EP 1514572 A2 3/2005
(Continued)

OTHER PUBLICATIONS

Australian Patent Application No. 2012340411 Examiner's First Report dated Jul. 14, 2016.
(Continued)

*Primary Examiner* — Kevin L Lee
(74) *Attorney, Agent, or Firm* — Wilson Sonsini Goodrich & Rosati

(57) ABSTRACT

A bag connector system includes a first coupling element, with a self-closing seal and a housing having a fluid inlet port and a fluid outlet port, and a second coupling element, with a housing having a fluid inlet end and a fluid outlet end. The fluid inlet end is configured to displace the self-closing seal when inserted into the fluid outlet port of the first coupling element. A bag connector system optionally includes a locking mechanism to maintain the first coupling element and second coupling element in a coupled state. Uncoupling of the first and second coupling elements results in minimal fluid contamination on the outer surfaces of the coupling elements. The bag connector systems provided herein are included in medical appliances for waste management.

22 Claims, 19 Drawing Sheets

Related U.S. Application Data

(60) Provisional application No. 61/861,357, filed on Aug. 1, 2013, provisional application No. 61/929,923, filed on Jan. 21, 2014.

(51) Int. Cl.
*F16L 37/38* (2006.01)
*F16L 37/46* (2006.01)
*A61F 5/44* (2006.01)
*A61M 39/26* (2006.01)

(52) U.S. Cl.
CPC ............. *A61M 39/26* (2013.01); *F16L 37/32* (2013.01); *F16L 37/38* (2013.01); *F16L 37/46* (2013.01); *A61M 2039/263* (2013.01); *Y10T 137/9029* (2015.04)

(56) References Cited

U.S. PATENT DOCUMENTS

| | | | |
|---|---|---|---|
| 3,127,148 A | 3/1964 | Collar | |
| 3,211,150 A | 10/1965 | Foderick | |
| 3,446,245 A | 5/1969 | Snyder, Jr. | |
| 3,721,726 A | 3/1973 | Schwartzman | |
| 3,777,757 A | 12/1973 | Gray et al. | |
| 4,116,201 A | 9/1978 | Shah | |
| 4,178,938 A | 12/1979 | Au | |
| 4,280,498 A | 7/1981 | Jensen | |
| 4,431,019 A | 2/1984 | Kopp et al. | |
| 4,541,457 A * | 9/1985 | Blenkush | F16L 37/0841 137/614.05 |
| 4,629,159 A | 12/1986 | Wellenstam | |
| 4,948,092 A | 8/1990 | Kasper et al. | |
| 4,955,879 A | 9/1990 | Mervine | |
| 5,350,364 A | 9/1994 | Stephens et al. | |
| 5,454,784 A | 10/1995 | Atkinson et al. | |
| 5,496,300 A | 3/1996 | Hirsch et al. | |
| 5,609,195 A * | 3/1997 | Stricklin et al. | F16L 37/28 137/614.04 |
| 5,628,726 A | 5/1997 | Cotter | |
| 5,709,244 A * | 1/1998 | Patriquin et al. | F16L 37/30 137/614.04 |
| 5,957,151 A | 9/1999 | Dalcourt et al. | |
| 6,045,542 A | 4/2000 | Cawood | |
| 6,050,973 A | 4/2000 | Duffy | |
| 6,146,374 A | 11/2000 | Erskine et al. | |
| 6,655,656 B2 * | 12/2003 | Maldays | F16L 37/23 137/614 |
| 7,261,125 B1 * | 8/2007 | Lien | F16L 37/098 137/614.04 |
| 7,727,188 B2 | 6/2010 | Machado et al. | |
| 8,016,816 B2 | 9/2011 | Gregory | |
| 8,052,671 B2 | 11/2011 | Christensen et al. | |
| 8,888,739 B2 | 11/2014 | Gregory et al. | |
| 9,623,201 B2 | 4/2017 | Gregory et al. | |
| 9,669,205 B2 | 6/2017 | Jin et al. | |
| 9,808,606 B2 | 11/2017 | Jin et al. | |
| 2003/0079752 A1 | 5/2003 | Hart et al. | |
| 2003/0106610 A1 * | 6/2003 | Roos et al. | B67D 1/0835 137/614.04 |
| 2003/0221728 A1 | 12/2003 | Enerson | |
| 2003/0229259 A1 | 12/2003 | Waksman et al. | |
| 2004/0010238 A1 | 1/2004 | Manera et al. | |
| 2004/0039374 A1 | 2/2004 | Tighe et al. | |
| 2004/0158197 A1 | 8/2004 | Bellhouse et al. | |
| 2004/0176703 A1 | 9/2004 | Christensen et al. | |
| 2005/0054996 A1 | 3/2005 | Gregory | |
| 2005/0082828 A1 | 4/2005 | Wicks et al. | |
| 2005/0101939 A1 | 5/2005 | Mitchell | |
| 2005/0124932 A1 | 6/2005 | Foster et al. | |
| 2005/0256460 A1 | 11/2005 | Rome et al. | |
| 2005/0273083 A1 | 12/2005 | Lebel et al. | |
| 2007/0123832 A1 | 5/2007 | Cline et al. | |
| 2007/0142700 A1 | 6/2007 | Fogarty et al. | |
| 2007/0149922 A1 | 6/2007 | Schneider et al. | |
| 2007/0215221 A1 * | 9/2007 | Lien | F16L 37/098 137/614.04 |
| 2008/0009794 A1 | 1/2008 | Bagaoisan et al. | |
| 2008/0103463 A1 | 5/2008 | Tsai et al. | |
| 2008/0114316 A1 | 5/2008 | Christensen et al. | |
| 2008/0147012 A1 | 6/2008 | Rome | |
| 2008/0175719 A1 | 7/2008 | Tracey et al. | |
| 2009/0163892 A1 | 6/2009 | McMichael et al. | |
| 2010/0191192 A1 | 7/2010 | Prasad et al. | |
| 2010/0217189 A1 | 8/2010 | Pepper | |
| 2010/0274189 A1 | 10/2010 | Kurth et al. | |
| 2011/0295236 A1 | 12/2011 | Gregory et al. | |
| 2013/0030387 A1 | 1/2013 | Williams et al. | |
| 2013/0071170 A1 * | 3/2013 | Mehus et al. | F16L 37/32 401/139 |
| 2014/0052063 A1 | 2/2014 | Gregory et al. | |
| 2014/0107572 A1 | 4/2014 | Jin et al. | |
| 2014/0276497 A1 | 9/2014 | Robinson et al. | |
| 2015/0051542 A1 | 2/2015 | Gregory et al. | |
| 2015/0059901 A1 | 3/2015 | Jin et al. | |
| 2016/0339227 A1 | 11/2016 | Tsai et al. | |
| 2017/0173310 A1 | 6/2017 | Gregory et al. | |
| 2017/0259046 A9 | 9/2017 | Jin et al. | |
| 2018/0229013 A1 | 8/2018 | Tsai | |

FOREIGN PATENT DOCUMENTS

| | | |
|---|---|---|
| EP | 3027266 A1 | 6/2016 |
| EP | 3297585 A1 | 3/2018 |
| JP | S52158920 U | 12/1977 |
| JP | S61192991 A | 8/1986 |
| JP | H0629590 Y2 | 8/1994 |
| JP | H09327519 A | 12/1997 |
| JP | H09512892 A | 12/1997 |
| JP | 2003502588 A | 1/2003 |
| JP | 2007523296 A | 8/2007 |
| JP | 2008117545 A | 5/2008 |
| WO | WO-8300070 A1 | 1/1983 |
| WO | WO-9530856 A1 | 11/1995 |
| WO | WO-2004045704 A2 | 6/2004 |
| WO | WO-2006/043883 | 4/2006 |
| WO | WO-2011100187 A1 | 8/2011 |
| WO | WO-2013074763 A1 | 5/2013 |
| WO | WO-2013109293 A1 | 7/2013 |
| WO | WO-2015017646 A1 | 2/2015 |
| WO | WO-2016187350 A1 | 11/2016 |
| WO | WO-2017075226 A1 | 5/2017 |

OTHER PUBLICATIONS

Chinese Patent Application No. 201280067212.0 Second Office Action dated Jul. 12, 2016.
Chinese Patent Application No. 201280067212.0 Third Office Action dated Feb. 27, 2017.
European Patent Application No. 12849279.0 Communication dated Aug. 18, 2016.
European Patent Application No. 12849279.0 Communication dated Mar. 23, 2016.
European Patent Application No. 14832568.1 Supplementary European Search Report dated Feb. 15, 2017.
Japanese Patent Application No. 2014-542455 Office Action dated Dec. 6, 2016.
JP S58-501012A (See WO 83/00070 A1) for English.
Mexican Patent Application No. MX/a/2014/005934 Office Action dated Jul. 14, 2016.
New Zealand Patent Application No. 727366 First Examiner's Report dated Jan. 17, 2017.
PCTUS2014/049115 International Preliminary Report on Patentability dated Feb. 11, 2016.
PCT/US2012/025420 International Preliminary Report on Patentability dated Aug. 21, 2013.
PCT/US2012/025420 International Search Report and Written Opinion dated Jun. 6, 2012.
PCT/US2012/065239 International Preliminary Report on Patentability dated May 20, 2014.

(56) References Cited

OTHER PUBLICATIONS

PCT/US2012/065239 International Search Report completed Mar. 8, 2013.
PCT/US2012/065239 Written Opinion completed Mar. 8, 2013.
PCT/US2014/049115 International Search Report completed Oct. 28, 2014.
PCT/US2014/049115 Written Opinion completed Oct. 28, 2014.
PCT/US2016/033147 International Search Report and Written Opinion dated Aug. 16, 2016.
ROC (Taiwan) Patent Application No. 101142959 Office Action dated Mar. 21, 2016.
Russian Patent Application No. 2014124144 Office Action dated Nov. 14, 2016.
Taiwan Patent Application No. 105113600 Office Action dated Jan. 16, 2017.
U.S. Appl. No. 13/877,890 Office Action dated Mar. 27, 2014.
U.S. Appl. No. 14/000,384 Office Action dated Sep. 11, 2014.
U.S. Appl. No. 14/341,647 Office Action dated May 5, 2016.
U.S. Appl. No. 14/449,035 Office Action dated Feb. 12, 2016.
U.S. Appl. No. 14/449,035 Office Action dated Sep. 14, 2016.
U.S. Appl. No. 14/745,312 Office Action dated Feb. 17, 2016.
Australia Patent Application No. 2017204860 Examination Report No. 1 dated May 29, 2018.
Australian Patent Application No. 2014296130 Office Action dated Apr. 13, 2018.
Russian Patent Application No. 2016107147 Office Action date Apr. 24, 2018.
Canadian Patent Application No. 2,855,366 Office Action dated Aug. 29, 2018.
Chinese Patent Application No. 201480043509.2 Office Action dated Aug. 30, 2018.
Japanese Patent Application No. 2016-531895 Office Action dated Jul. 10, 2018.
New Zealand Patent Application No. 727366 Office Action dated Aug. 20, 2018.
New Zealand Patent Application No. 744299 Office Action dated Aug. 20, 2018.
PCT/US2016/059132 International Preliminary Report on Patentability dated May 1, 2018.
PCT/US2016/059132 International Search Report and Written Opinion dated Jan. 6, 2017.
U.S. Appl. No. 15/158,426 Office Action dated Aug. 27, 2018.
EP16797245.4 Extended European Search Report dated Nov. 12, 2018.
U.S. Appl. No. 15/448,274 Restriction Requirement dated Nov. 15, 2018.
Australia Patent Application No. 2017200016 Examination Report No. 1 dated Nov. 14, 2017.
Japanese Patent Application No. 2014-542455 Office Action dated Nov. 14, 2017.
PCT/US2016/033147 International Preliminary Report on Patentability dated Nov. 30, 2017.
Japanese Patent Application No. 2016-531895 Office Action dated Jun. 11, 2019.

\* cited by examiner

Half-section view

Exploded view

SELF-CLOSING BAG CONNECTOR

CROSS-REFERENCE

This application is a continuation of application Ser. No. 14/449,035, filed Jul. 31, 2014, issued as U.S. Pat. No. 9,669,205 on Jun. 6, 2017, which claims the benefit of U.S. Application Ser. No. 61/861,357, filed Aug. 1, 2013; and U.S. Application Ser. No. 61/929,923, filed Jan. 21, 2014, each of which is incorporated herein by reference in their entirety.

BACKGROUND OF THE INVENTION

Bag connector systems are used in a wide range of medical appliances to connect medical grade tubing to an external fluid collection bag. Such fluid is liquid or semi-liquid in nature, for example, containing particulates or other solid material. Collected fluid includes waste fluid, including liquid or semi-liquid feces, urine or other bodily fluid. It is desirable to design a bag connector system that is easy to use, manipulatable, and hygienic.

SUMMARY OF THE INVENTION

In one aspect, disclosed herein are bag connector systems comprising a first coupling element comprising a housing having a fluid inlet port and a fluid outlet port, the first coupling element further comprising a self-closing seal to prevent fluid flow from exiting the fluid outlet port; and a second coupling element comprising a housing having a fluid inlet end and a fluid outlet end, the fluid inlet end configured to displace the self-closing seal when inserted into the fluid outlet port of the first coupling element; wherein uncoupling of the first coupling element and the second coupling element results in minimal fluid contamination on the outer surfaces of the coupling elements. In some embodiments, each of the first coupling element and the second coupling element further comprises a means to maintain the first coupling element and the second coupling element in a coupled state. In some embodiments, the self-closing seal is positioned within the housing of the first coupling element. In other embodiments, the self-closing seal is positioned outside of the housing of the first coupling element.

In some embodiments, the self-closing seal comprises a flapper connected to a leaf spring. In further embodiments, the housing of the first coupling element further comprises a washer. In some embodiments, each of the first coupling element and the second coupling element further comprises a means to maintain the first coupling element and the second coupling element in a coupled state. In further embodiments, the means to maintain the first coupling element and the second coupling element in a coupled state comprises a twist lock-in mechanism.

In some embodiments, the self-closing seal comprises a sliding cover connected to a spring element. In further embodiments, the housing of the first coupling element further comprises a washer. In some embodiments, the first coupling element further comprises at least one O-ring. In some embodiments, each of the first coupling element and the second coupling element further comprises a means to maintain the first coupling element and the second coupling element in a coupled state. In further embodiments, the means to maintain the first coupling element and the second coupling element in a coupled state comprises a cantilever snap-fit mechanism, including a single cantilever snap-fit mechanism. In other embodiments, the means to maintain the first coupling element and the second coupling element in a coupled state comprises a twist lock-in mechanism. In some embodiments, the second coupling element further comprises an O-ring positioned on the outer surface of the housing. In some embodiments, the second coupling element further comprises a check valve. In further embodiments, the check valve is a duckbill valve.

In some embodiments, the self-closing seal comprises a spring-loaded valve. In further embodiments, the spring-loaded valve comprises a spring seat, a spring element, and a flat cover. In still further embodiments, the spring-loaded valve is a poppet valve. In some embodiments, each of the first coupling element and the second coupling element further comprises a means to maintain the first coupling element and the second coupling element in a coupled state. In some embodiments, the second coupling element further comprises a sliding cover positioned over the fluid inlet port. In some embodiments, the second coupling element further comprises at least one O-ring. In some embodiments, each of the first coupling element and the second coupling element further comprises a means to maintain the first coupling element and the second coupling element in a coupled state. In further embodiments, the means to maintain the first coupling element and the second coupling element in a coupled state comprises a at least one cantilever snap, preferably a plurality of cantilever snaps, at the fluid outlet port of the first coupling element which forms a snap-fit with the sliding cover on the second coupling element.

In some embodiments, the self-closing seal between a first coupling element and second coupling element comprises a spring-loaded connector. In further embodiments, the first coupling element comprises a tube-connector base, a spring element, a sliding cover, at least one O-ring and a cap. In some embodiments, the tube-connector base comprises a fluid inlet port and a fluid outlet port. In other embodiments, the second coupling element comprises a bag connector base, a duckbill valve and a valve holder. In yet other embodiments, the bag-connector base comprises a fluid inlet port and a fluid outlet port. In some embodiments, when disconnected both connectors are in closed status, closing the drainage path within the first coupling element. In some embodiments, when connected the end of the valve holder within the second coupling element may push against the first flange of the sliding cover in the first coupling element until the side opening on the connector base of the first coupling element is exposed. In other embodiments, upon opening of the sliding cover in the first coupling element, the valve (optionally a duckbill valve) may be pushed open by the cap and base body of the second coupling element. Upon opening by the cap and base body of the second coupling element, the drainage path on both sides becomes open for drainage. In yet other embodiments, upon disconnection of the first coupling element and the second coupling element, the spring element may push the sliding cover of the first coupling element into position to close off the drainage path. Upon disconnection and closing of the drainage path, the duckbill valve may also remain closed.

In another aspect, disclosed herein are medical appliances comprising a fluid storage container and a bag connector system, the bag connector system comprising a first coupling element comprising a housing having a fluid inlet port and a fluid outlet port, the first coupling element further comprising a self-closing seal to prevent fluid flow from exiting the fluid outlet port; and a second coupling element comprising a housing having a fluid inlet end and a fluid outlet end, the fluid inlet end configured to displace the self-closing seal when inserted into the fluid outlet port of the first coupling element; and wherein the fluid outlet end of the second coupling element is connected to the fluid storage container and uncoupling of the first coupling element and the second coupling element results in minimal fluid contamination on the outer surfaces of the coupling elements. In some embodiments, the self-closing seal is a flapper connected to a leaf spring, a sliding cover connected to a spring element, or a spring-loaded valve. In some embodiments, the second coupling element further comprises a check valve. In further embodiments, the check valve is a duckbill valve. In some embodiments, each of the first coupling element and the second coupling element further comprises a means to maintain the first coupling element and the second coupling element in a coupled state. In further embodiments, the means to maintain the first coupling element and the second coupling element in a coupled state is selected from a twist lock-in mechanism; a single cantilever snap-fit mechanism; and a cantilever snap-fit mechanism comprising a plurality of cantilever snaps at the fluid outlet port of the first coupling element which forms a snap-fit with the sliding cover on the second coupling element.

DETAILED DESCRIPTION OF THE INVENTION

Figure 1:
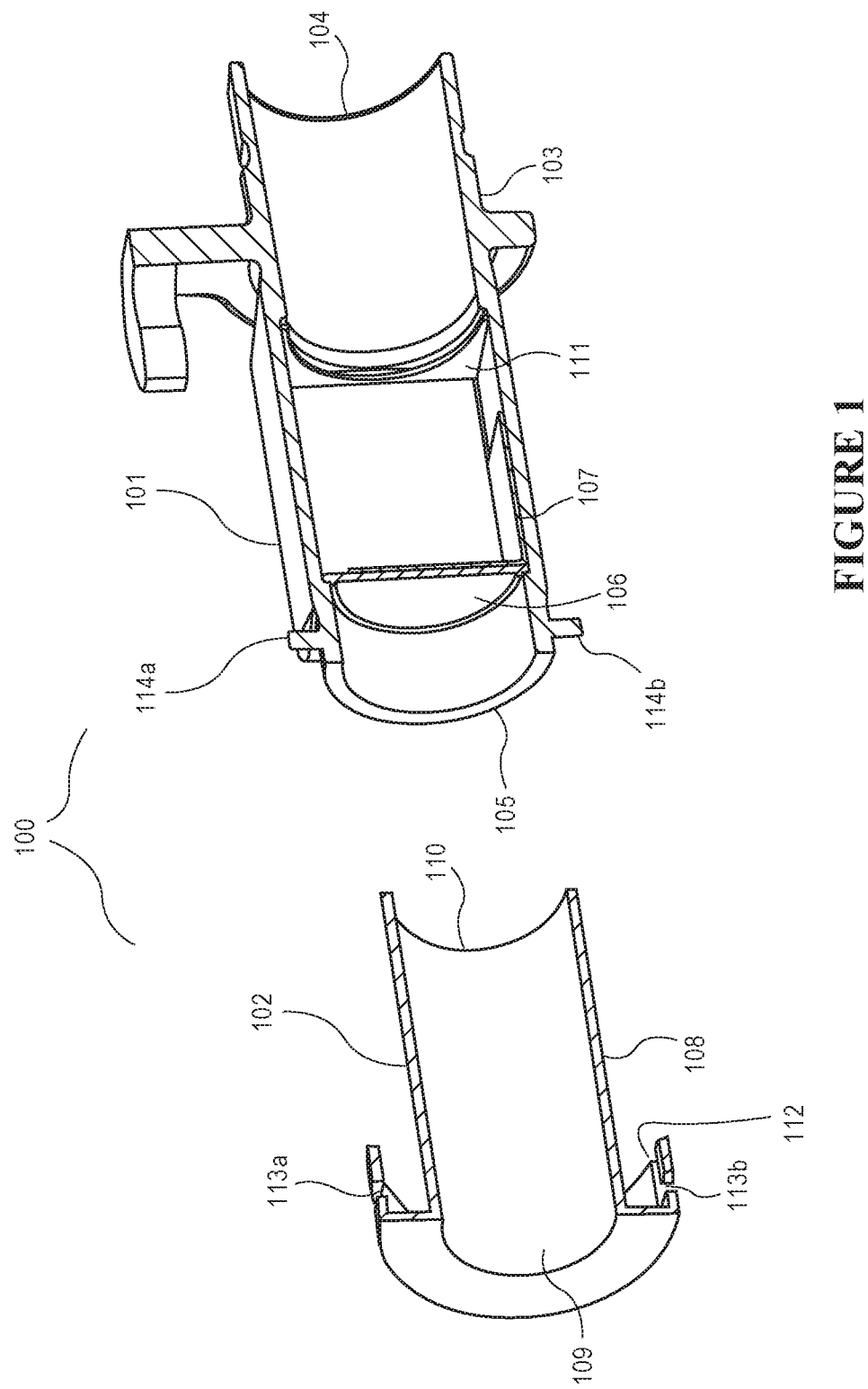
FIG. 1 illustrates a schematic cross-sectional view of a first embodiment of a bag connector system; in this particular figure, the coupling elements are aligned for coupling and the bag connector system is in the uncoupled state.
Figure 2A:
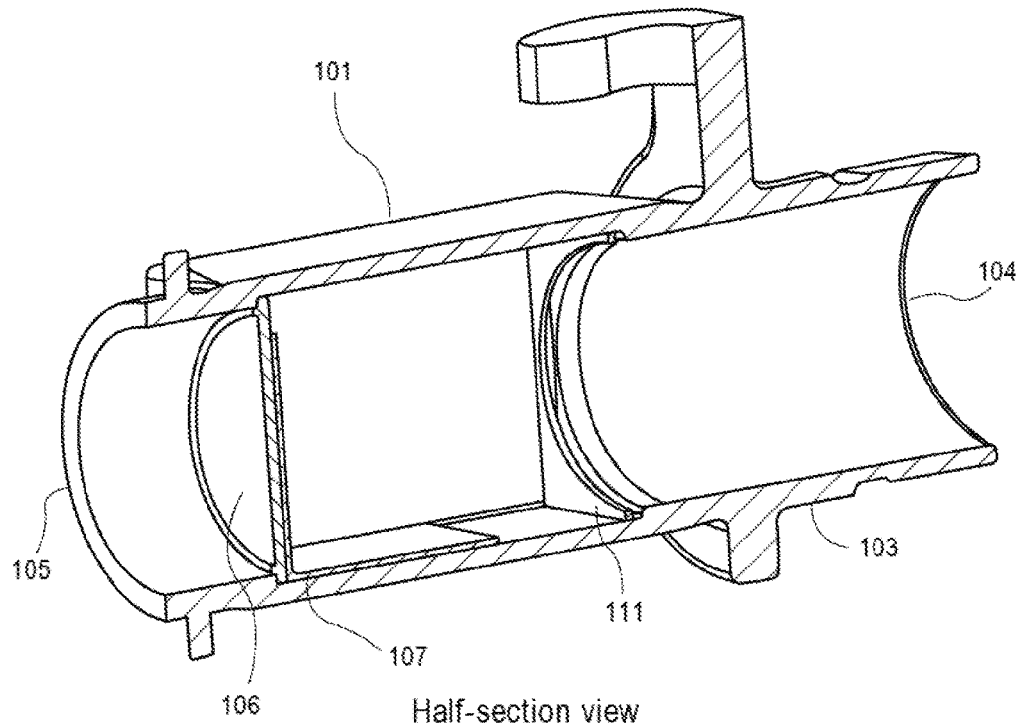
FIG. 2a illustrates a schematic cross-sectional view of the first coupling element of the bag connector system of FIG. 1.
Figure 2B:
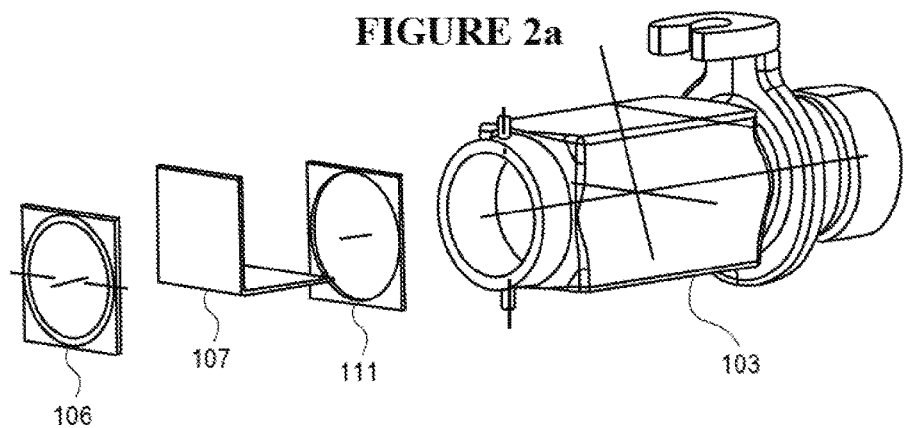
FIG. 2b illustrates an exploded view of the first coupling element of the bag connector system of FIG. 1.
Figure 2C:
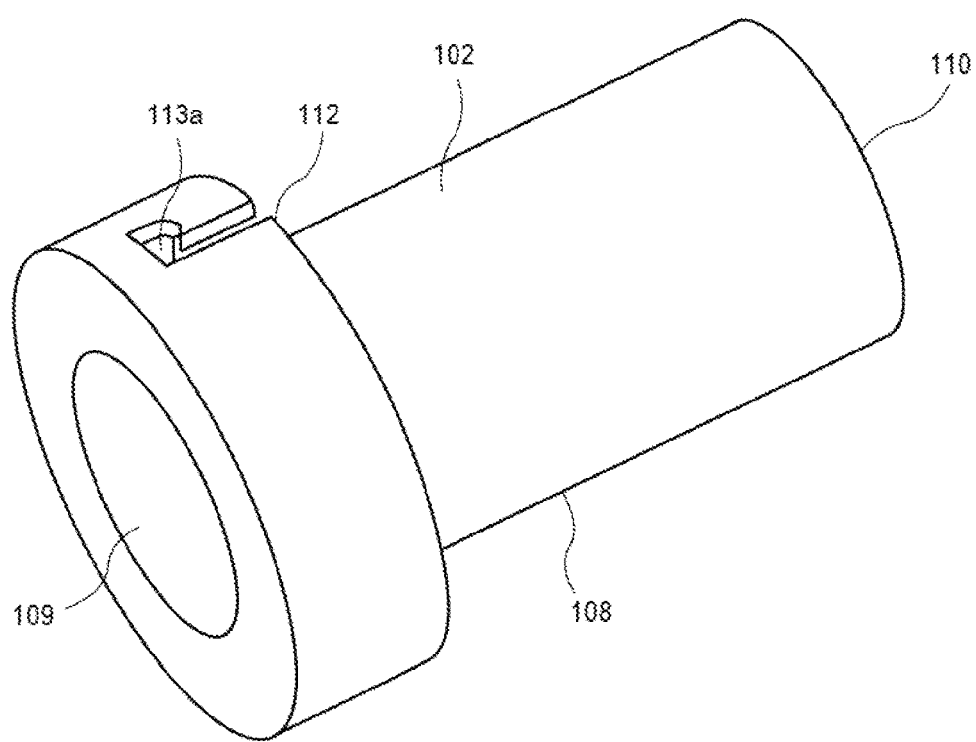
FIG. 2c illustrates a perspective view of the second coupling element of the bag connector system of FIG. 1.

Provided herein are bag connector systems to be used in a medical appliance. These bag connector systems provide a simple method to connect tubing that directs the flow of waste to an external waste collection bag while minimizing the exposure of the waste inside the tubing to the outside environment. When the two coupling elements of the bag connector system are coupled together, the drainage path between the tubing and the waste collection bag is activated to open. When the two coupling elements of the bag connector system are uncoupled or disconnected, the coupling element attached to the tubing will automatically close to contain the waste in the tubing and in the coupling element attached to the tubing. As such, the outer surfaces of the coupling element attached to the tubing will have minimum exposure of the contamination of the waste.

Medical Appliance with Bag Connector System

Disclosed herein, in certain embodiments, are medical appliances for the management of fecal or urinary waste. In some embodiments, the medical appliances comprise a catheter, an external waste storage container, and a bag connector system that connects the catheter to the external waste storage container. In further embodiments, the connection to the bag connector system is through the use of medical grade tubing. In other embodiments, the bag connector system is directly connected to the external waste storage container and/or to the catheter. In some embodiments, the medical grade tubing is draining tubing from the catheter. In some embodiments, the catheter is a rectal catheter. In other embodiments, the catheter is a urinary catheter.

In some embodiments, the medical appliances comprise a catheter, an external waste collection container, an external waste storage container, and a bag connector system that connects the waste collection container to the waste storage container. In further embodiments, the connection to the bag connector system is through the use of medical grade tubing. In other embodiments, the bag connector system is directly connected to the external waste collection container and/or external waste storage container. In some embodiments, the catheter is a rectal catheter. In other embodiments, the catheter is a urinary catheter.

In some embodiments, the bag connector system comprises a first coupling element comprising a housing having a fluid inlet port and a fluid outlet port, the first coupling element further comprising a self-closing seal to prevent fluid flow from exiting the fluid outlet port; and a second coupling element comprising a housing having a fluid inlet end and a fluid outlet end, the fluid inlet end configured to displace the self-closing seal when inserted into the fluid outlet port of the first coupling element. In some embodiments, the self-closing seal is positioned within the housing of the first coupling element. In other embodiments, the self-closing seal is positioned outside of the housing of the first coupling element.

Disclosed herein, in certain embodiments, are medical appliances comprising a fluid storage container and a bag connector system, the bag connector system comprising a first coupling element comprising a housing having a fluid inlet port and a fluid outlet port, the first coupling element further comprising a self-closing seal to prevent fluid flow from exiting the fluid outlet port; and a second coupling element comprising a housing having a fluid inlet end and a fluid outlet end, the fluid inlet end configured to displace the self-closing seal when inserted into the fluid outlet port of the first coupling element; and wherein the fluid outlet end of the second coupling element is connected to the fluid storage container and uncoupling of the first coupling element and the second coupling element results in minimal fluid contamination on the outer surfaces of the coupling elements. In some embodiments, the self-closing seal is positioned within the housing of the first coupling element. In other embodiments, the self-closing seal is positioned outside of the housing of the first coupling element.

In some embodiments, the self-closing seal is a duckbill valve, a flapper connected to a leaf spring, a sliding cover connected to a spring element, or a spring-loaded valve.

In some embodiments, each of the first coupling element and the second coupling element further comprises a means to maintain the first coupling element and the second coupling element in a coupled state. In further embodiments, the means to maintain the first coupling element and the second coupling element in a coupled state is selected from an interference fit mechanism, a twist lock-in (bayonet latch) mechanism, an annular snap-fit mechanism, a single cantilever snap-fit mechanism, and a multiple cantilever snap-fit mechanism comprising a plurality of cantilever snaps at the fluid outlet port of the first coupling element which forms a snap-fit with the sliding cover on the second coupling element. In still further embodiments, the means to maintain the first coupling element and the second coupling element in a coupled state is selected from a twist lock-in mechanism, a single cantilever snap-fit mechanism, and a multiple cantilever snap-fit mechanism comprising a plurality of cantilever snaps at the fluid outlet port of the first coupling element which forms a snap-fit with the sliding cover on the second coupling element.

In some embodiments, the medical grade tubing is made of silicone, PVC, rubber, polyurethane, or other suitable material. In various embodiments, the medical grade tubing can have an inner diameter of 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19, 20, 21, 22, 23, 24, 25 millimeters, or more, including increments therein.

Bag Connector System

Disclosed herein, in certain embodiments, are medical devices for the management of fecal or urinary waste. In some embodiments, a medical device disclosed herein comprises a bag connector system. In further embodiments, a bag connector system comprises a first coupling element comprising a housing having a fluid inlet port and a fluid outlet port, the first coupling element further comprising a self-closing seal to prevent fluid flow from exiting the fluid outlet port; and a second coupling element comprising a housing having a fluid inlet end and a fluid outlet end, the fluid inlet end configured to displace the self-closing seal when inserted into the fluid outlet port of the first coupling element. In still further embodiments, the self-closing seal allows the uncoupling of the first coupling element and the second coupling element to result in minimal fluid contamination on the outer surfaces of the coupling elements. In some embodiments, the self-closing seal is positioned within the housing of the first coupling element. In other embodiments, the self-closing seal is positioned outside of the housing of the first coupling element.

In some embodiments, minimal fluid contamination on the outer surfaces of the coupling elements upon uncoupling of the first coupling element and second coupling element is little to no detectable fluid contamination on the outer surfaces of the coupling elements. In some embodiments, minimal fluid contamination on the outer surfaces of the coupling elements upon uncoupling of the first coupling element and second coupling element is negligible or limited fluid contamination on the outer surfaces of the coupling elements. In some embodiments, minimal fluid contamination on the outer surfaces of the coupling elements upon uncoupling of the first coupling element and second coupling element is little to no detectable fluid contamination to negligible or limited fluid contamination on the outer surfaces of the coupling elements.

In some embodiments, the housing of the coupling element is made of plastic or any other suitable material for containing and directing fluid, or a combination of such suitable materials.

In some embodiments, the self-closing seal is a check valve or a sliding cover connected to a spring element. In some embodiments, the self-closing seal is a duckbill valve, a flapper connected to a leaf-spring; a sliding cover connected to a spring element, or a spring-loaded valve. In some embodiments, the sliding cover and spring element are joined to form a unitary object. In other embodiments, the sliding cover and spring element are separate objects in direct contact with one another.

In some embodiments, the self-closing seal is a check valve. In some embodiments, the check valve is a ball check valve, a diaphragm check valve, a swing check valve, a stop-check valve, a lift-check valve, an in-line check valve or a duckbill valve. In some embodiments, the check valve is a ball check valve. In some embodiments, the check valve is a diaphragm check valve. In some embodiments, the check valve is a swing check valve. In some embodiments, the check valve is a stop-check valve. In some embodiments, the check valve is a lift-check valve. In some embodiments, the check valve is an in-line check valve. In some embodiments, the check valve is a leaf valve. In some embodiments, the check valve is a duckbill valve.

In some embodiments, the self-closing seal is a flapper connected to a leaf-spring; a sliding cover connected to a spring element, or a spring-loaded valve.

In some embodiments, the self-closing seal is a flapper connected to a leaf-spring. In some embodiments, the flapper is made of rubber or other elastomer. In some embodiments, the leaf-spring is made of metal, plastic, rubber, or other elastomer. In some embodiments, the flapper and the leaf-spring are an integrated piece or may comprise separately manufactured pieces joined together.

In some embodiments, the self-closing seal is a sliding cover connected to a spring element. In some embodiments, the sliding cover is made of plastic or other suitable material. In some embodiments, the spring element is made of metal, plastic, or rubber.

In some embodiments, the self-closing seal is a spring-loaded valve. In further embodiments, the spring-loaded valve comprises a spring seat, a spring element, and a flat cover. In still further embodiments, the spring-loaded valve is a poppet valve. In some embodiments the spring-loaded valve is an integrated piece or may comprise separately manufactured pieces joined together. In some embodiments, the spring seat is made of plastic or metal. In some embodiments, the spring element is made of plastic or metal. In some embodiments, the flat cover is made of silicone, rubber, or other elastomer.

In some embodiments, each of the first coupling element and the second coupling element further comprises a means to maintain the first coupling element and the second coupling element in a coupled state. In some embodiments, the means to maintain the first coupling element and the second coupling element in a coupled state is a locking mechanism. In some embodiments, the locking mechanism is selected from a twist lock-in (bayonet latch) mechanism, a single cantilever snap-fit mechanism, a multiple cantilever snap-fit mechanism, an annular snap-fit mechanism, or an interference fit mechanism. In some embodiments, the locking mechanism is a twist lock-in mechanism. In some embodiments, the locking mechanism is a single cantilever snap-fit mechanism. In some embodiments, the locking mechanism comprises a plurality of cantilever snaps at the fluid outlet port of the first coupling element which forms a snap-fit with the sliding cover on the second coupling element. In some embodiments, the first coupling element and the second coupling element further comprises complementary components of a locking mechanism. In further embodiments, components of a locking mechanism are part of the fluid outlet port of the first coupling element and part of the fluid inlet end of the second coupling element. In some embodiments, the first coupling element further comprises a washer. In some embodiments, the washer is made of silicone, fiber, rubber, or other elastomer. In some embodiments, the washer is a flat ring with a polyhedral or circular shape and a circular central opening. In some embodiments, the washer is a tapered ring.

In some embodiments the second coupling element further comprises at least one O-ring. In some embodiments, the second coupling element further comprises an O-ring positioned on the outer surface of the housing. In some embodiments, the O-ring is made of silicone, rubber, or other elastomer.

In some embodiments, the second coupling element further comprises a sliding cover positioned over the fluid inlet port. In some embodiments, the sliding cover is made of plastic or other suitable material, or combination of such materials. In some embodiments, the sliding cover is self-closing and is connected to a spring element.

In some embodiments, the second coupling element further comprises a check valve. In some embodiments, the check valve is a ball check valve, a diaphragm check valve, a swing check valve, a stop-check valve, a lift-check valve, an in-line check valve or a duckbill valve. In some embodiments, the check valve is a ball check valve. In some embodiments, the check valve is a diaphragm check valve. In some embodiments, the check valve is a swing check valve. In some embodiments, the check valve is a stop-check valve. In some embodiments, the check valve is a lift-check valve. In some embodiments, the check valve is an in-line check valve. In some embodiments, the check valve is a leaf valve. In some embodiments, the check valve is a duckbill valve.

Referring to FIGS. 1, 2a-c, and 3a-b, a first embodiment of a bag connector system 100 comprises a first coupling element 101 and a second coupling element 102. The first coupling element 101 comprises a housing 103 having a fluid inlet port 104 and a fluid outlet port 105. The second coupling element 102 comprises a housing 108 having a fluid outlet end 109 and a fluid inlet end 110. Housing 103 and housing 108 may be made of plastic or any material suitable for containing and directing fluid.

The first coupling element 101 also comprises a flapper 106 attached to a leaf spring 107. The flapper 106 may be made of resilient material such as rubber or other elastomer. The leaf spring 107 may be made of metal, plastic, rubber or other elastomer. The flapper 106 and the leaf spring 107 can be an integrated piece made of metal, plastic, elastomer and other suitable material, or may comprise two separately manufactured pieces joined together.

Referring to FIG. 1, in the uncoupled state of the bag connector system 100, the flapper 106 automatically provides a seal within the housing 103 that prevents the exit of fluid from the housing 103 through the fluid outlet port 105. The leaf spring 107 provides slight compression to the flapper 106 to automatically place the flapper 106 in this sealed position when in its uncoupled state, and to maintain this sealed position.

Figure 3A:
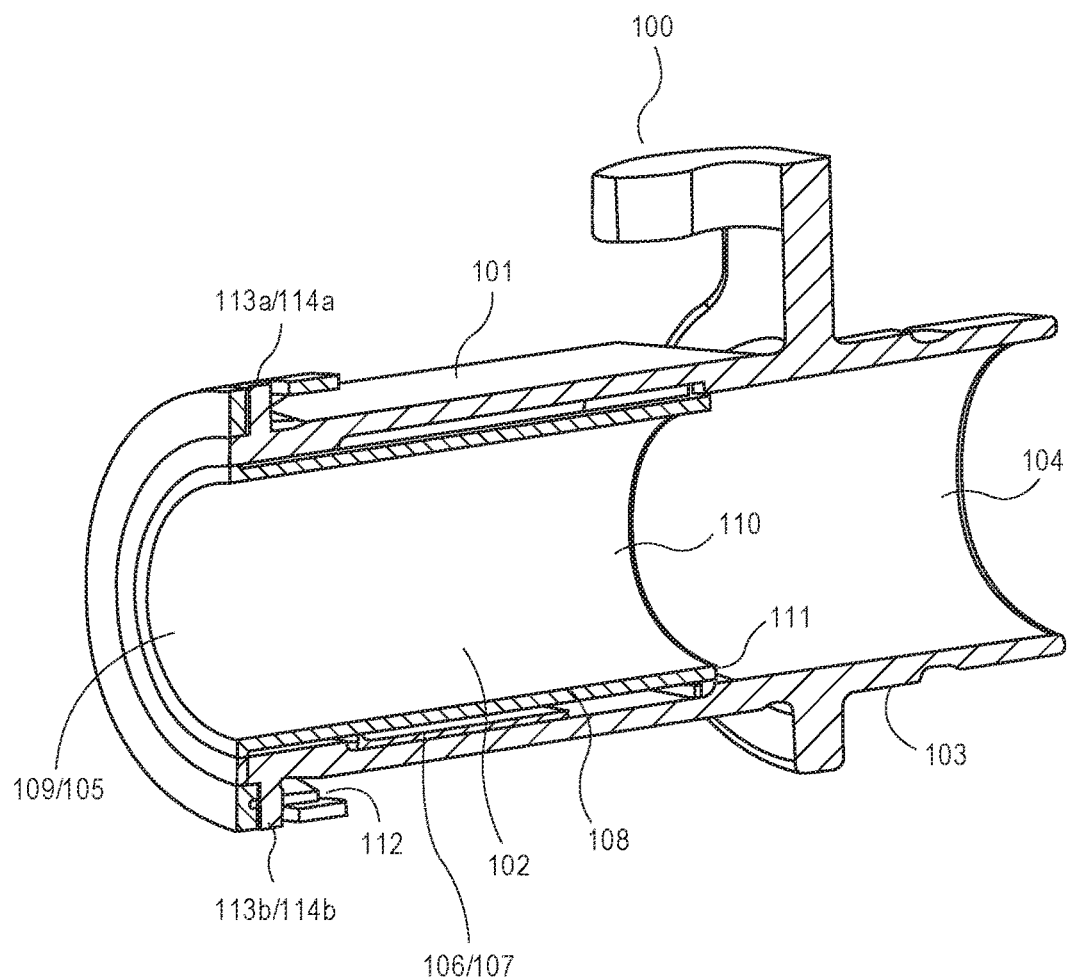
FIG. 3a illustrates a schematic cross-sectional view of the bag connector system of FIG. 1; in this particular figure, the coupling elements are coupled, the washer is a flat ring, and the bag connector system is in the coupled state.

Referring to FIG. 3a, in the coupled state of the bag connector system 100, the flapper 106 is obstructed by the second coupling element 102. The fluid inlet end 110 of the second coupling element 102 pushes against the flapper 106, partially or completely obstructing the flapper 106 and eliminating the seal which was created and maintained by the flapper and leaf-spring mechanisms during the uncoupled state. In this way, fluid within the housing 103 can flow through the coupled bag connector system 100 and be collected in a fluid storage container connected to the fluid outlet end 109 of the second coupling element 102.

Figure 3B:
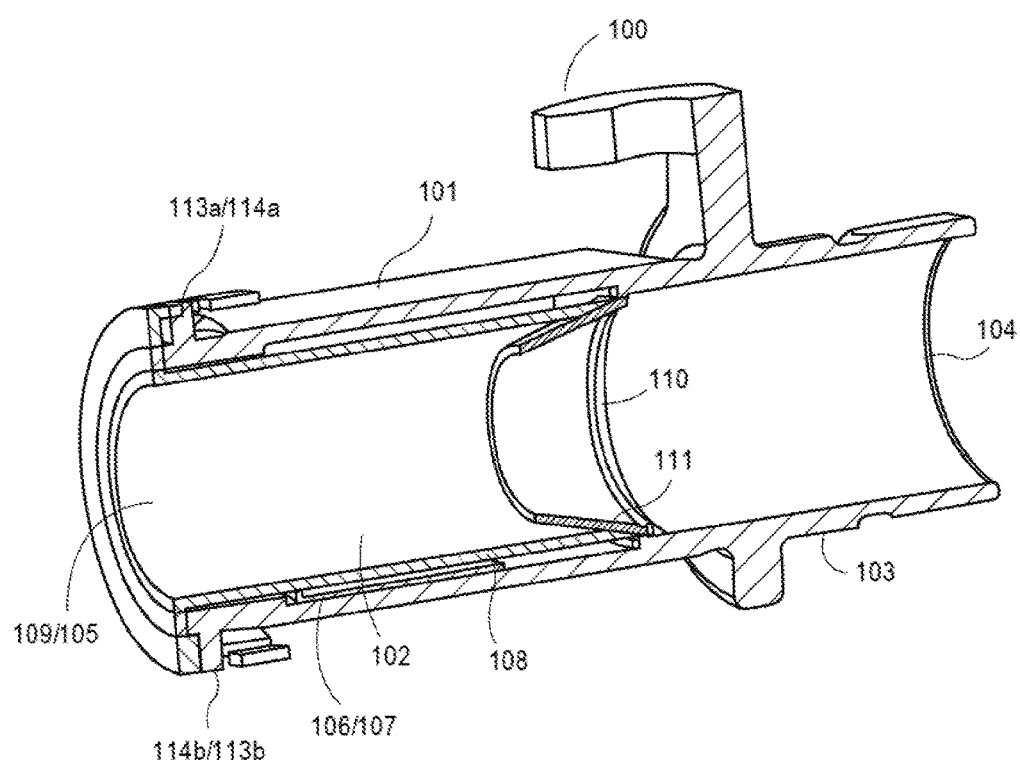
FIG. 3b illustrates a schematic cross-sectional view of an alternative embodiment of the bag connector system of FIG. 3a; in this particular figure, the washer is a tapered ring.

The first coupling element 101 may further comprise a washer 111 that interacts with the second coupling element 102 during the coupled state to create and maintain a seal between the second coupling element 102 and the first coupling element 101. Referring to FIGS. 3a and 3b, the fluid inlet end 110 of the second coupling element 102 comes in contact with the washer 111 to create this seal. The washer 111 may be made of silicone, rubber, or another elastomer. In terms of shape, the washer may be a ring (FIG. 3a) or a tapered ring (FIG. 3b).

Each of the first coupling element 101 and the second coupling element 102 further comprises complementary components of a locking mechanism, which maintains the first coupling element and the second coupling element in a coupled state. Such locking mechanisms include a twist lock-in mechanism, bayonet latch, or other locking mechanism which maintains a coupled state between the first coupling element and the second coupling element. For example, in one embodiment the external edge of the fluid outlet end 109 of the second coupling element 102 is a rotatable locking member 112 having two slots 113a and 113b which receive pins 114a and 114b located on the outer surface of the fluid outlet port 105. When the twist lock-in mechanism is in a first position, the pins 114a and 114b can pass through the complementary slots 113a and 113b, easily coupling or uncoupling the first coupling element 101 and the second coupling element 102. When the twist lock-in mechanism is in a second position, the pins 114a and 114b cannot pass through the complementary slots 113a and 113b, maintaining the first coupling element 101 and the second coupling element 102 in a coupled state. The twist lock-in mechanism is toggled between the first and second positions by rotating the coupled coupling elements in opposing directions along the axis of the fluid flow pathway.

Referring to FIGS. 4, 5a-c, 6, and 7, a second embodiment of a bag connector system 200 comprises a first coupling element 201 and a second coupling element 202. The first coupling element 201 comprises a housing 203 having a fluid inlet port 204 and a fluid outlet port 205. The second coupling element 202 comprises a housing 208 having a fluid outlet end 209 and a fluid inlet end 210. Housing 203 and housing 208 may be made of plastic or any material suitable for containing and directing fluid.

The first coupling element 201 also comprises a sliding cover 206 attached to a spring element 207. Like housing 203, the sliding cover 206 may be made of plastic or any suitable material. The spring element 207 may be made of metal, plastic, or rubber.

Figure 4:
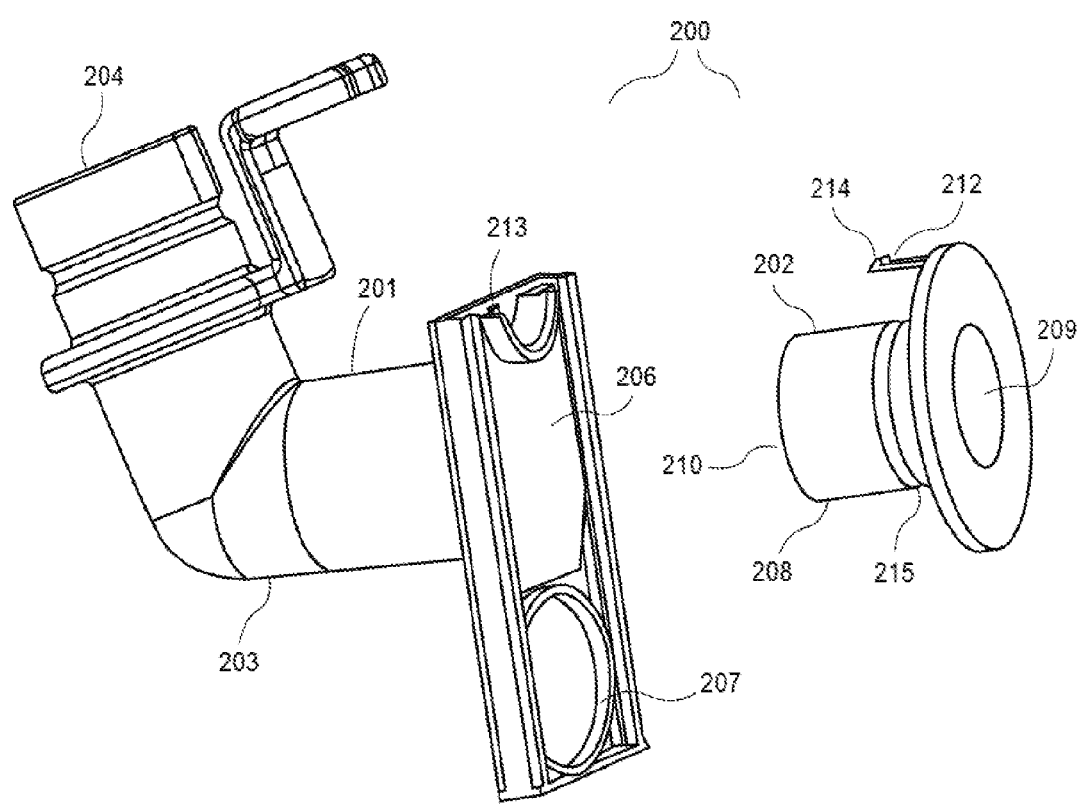
FIG. 4 illustrates a perspective view of a second embodiment of a bag connector system; in this particular figure, the coupling elements are aligned for coupling and the bag connector system is in the in the uncoupled state
Figure 5A:
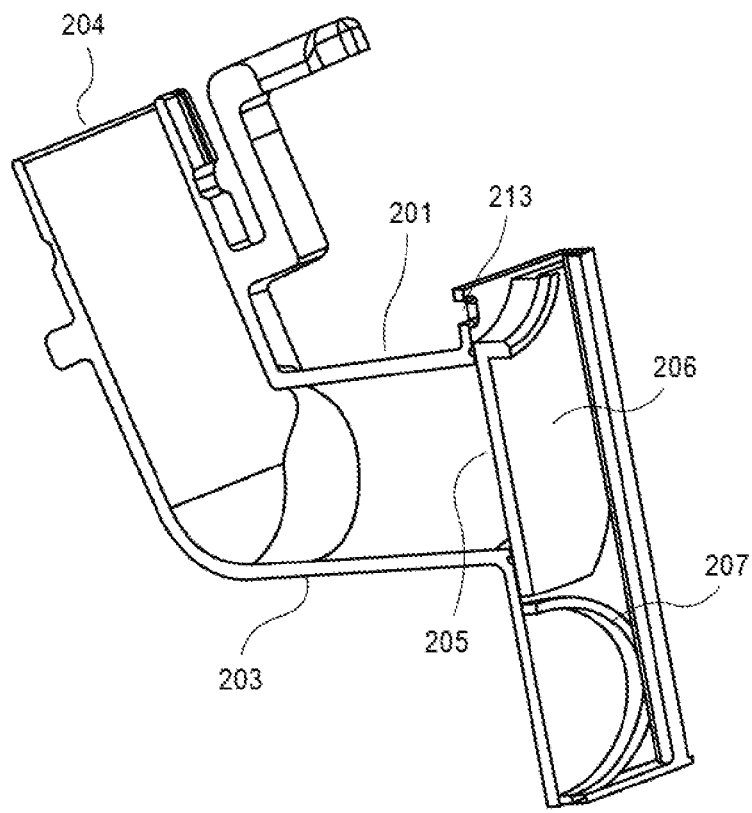
FIG. 5a illustrates a schematic cross-sectional view of the first coupling element of the bag connector system of FIG. 4.
Figure 5B:
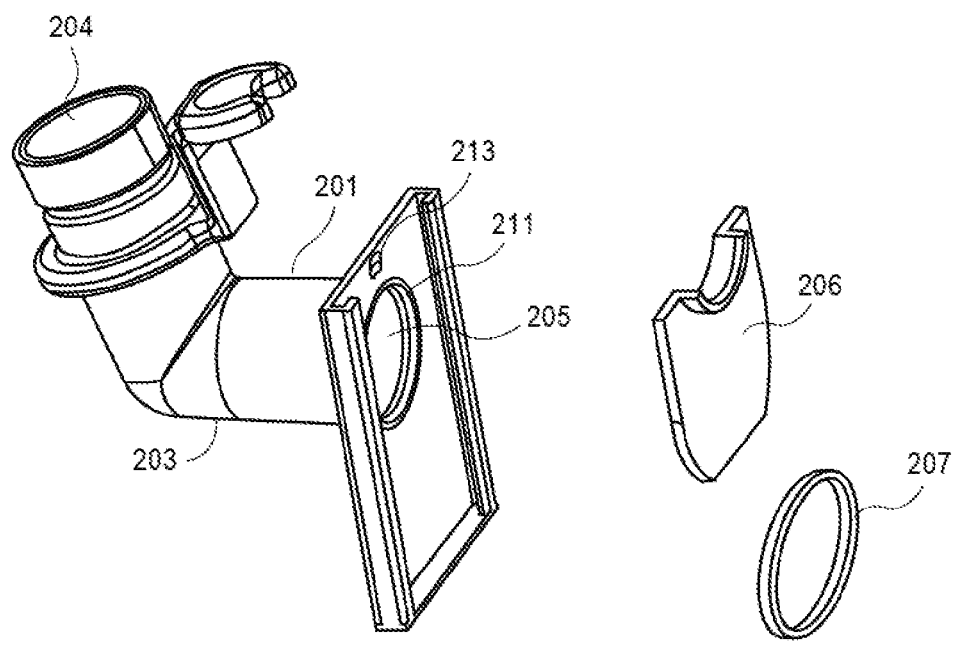
FIG. 5b illustrates an exploded view of the first coupling element of the bag connector system of FIG. 4.
Figure 5C:
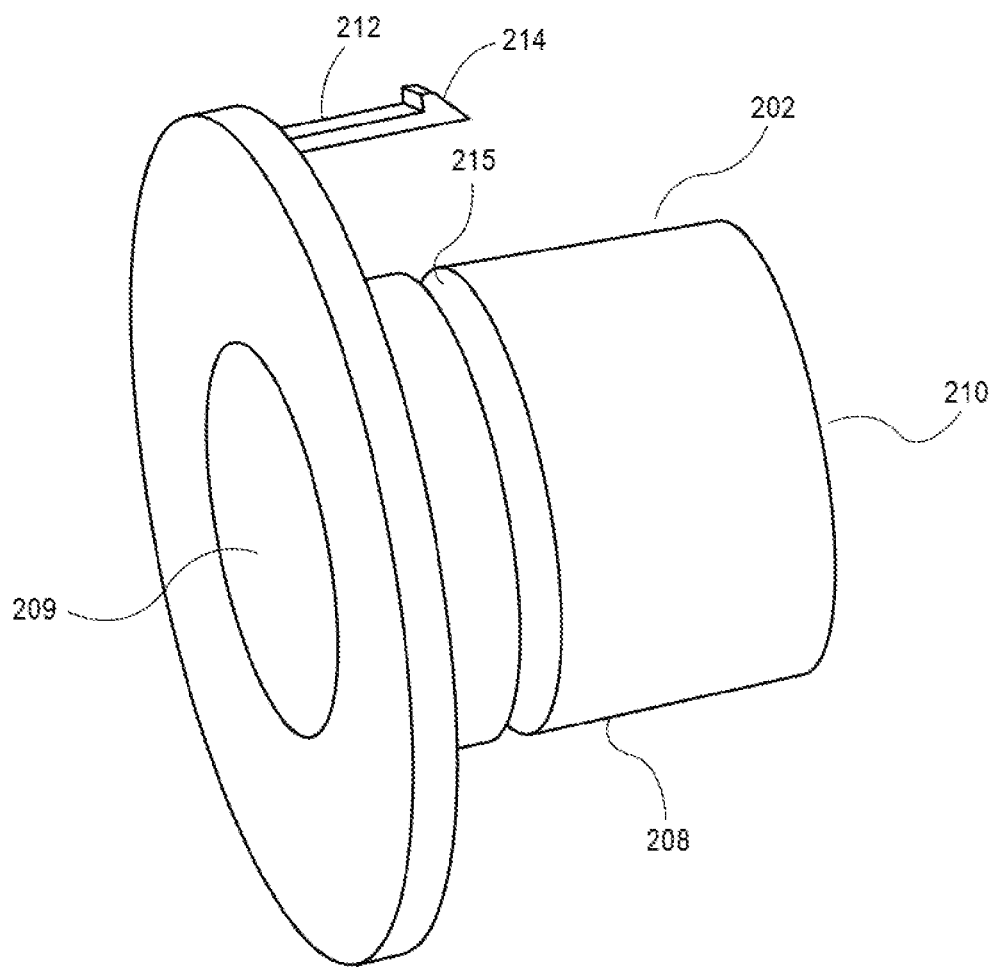
FIG. 5c illustrates a perspective view of the second coupling element of the bag connector system of FIG. 4

Referring to FIG. 4, in the uncoupled state of the bag connector system 200, the sliding cover 206 completely covers the fluid outlet port 205, preventing the exit of fluid from the housing 203 through the fluid outlet port 205. The spring element 207 provides slight compression to the sliding cover 206 to automatically place the sliding cover 206 over fluid outlet port 205 and maintain this sealed position in its uncoupled state.

Figure 6:
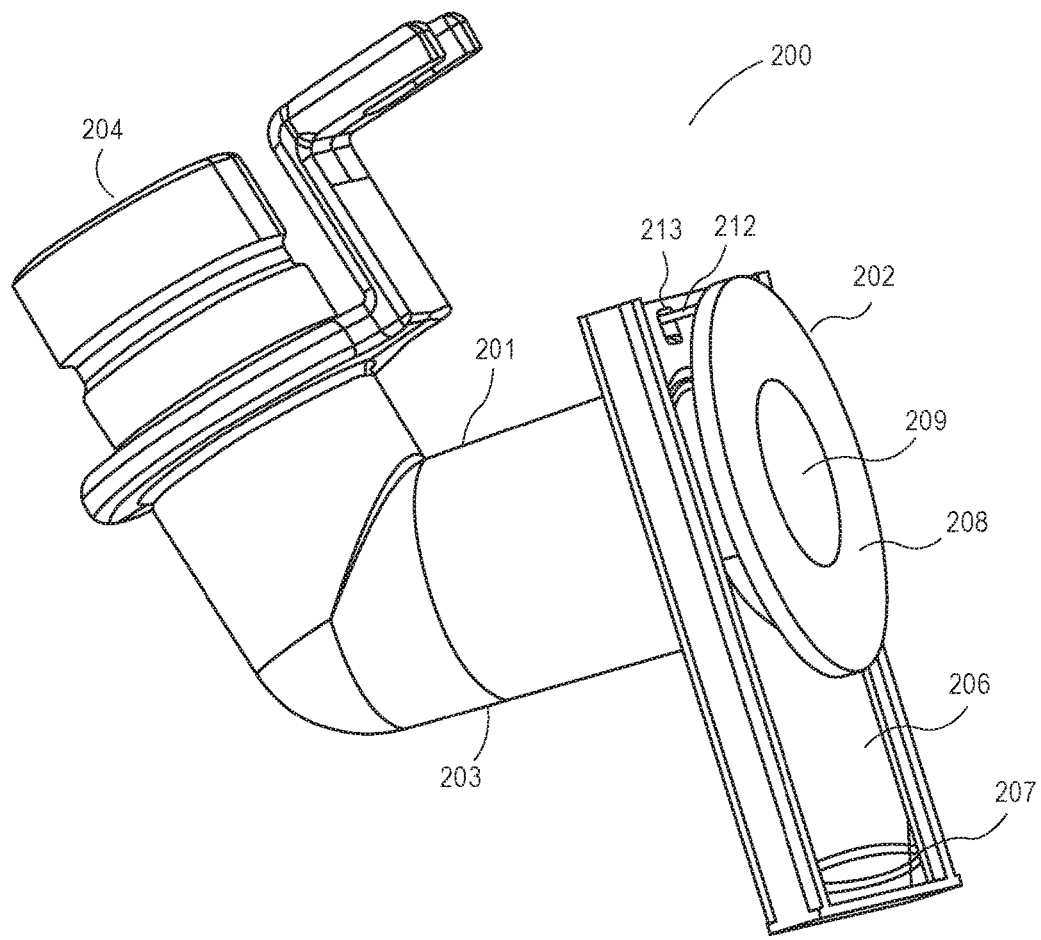
FIG. 6 illustrates a perspective view of the bag connector system of FIG. 4; in this particular figure, the coupling elements are coupled and the bag connector system is in the coupled state.
Figure 7:
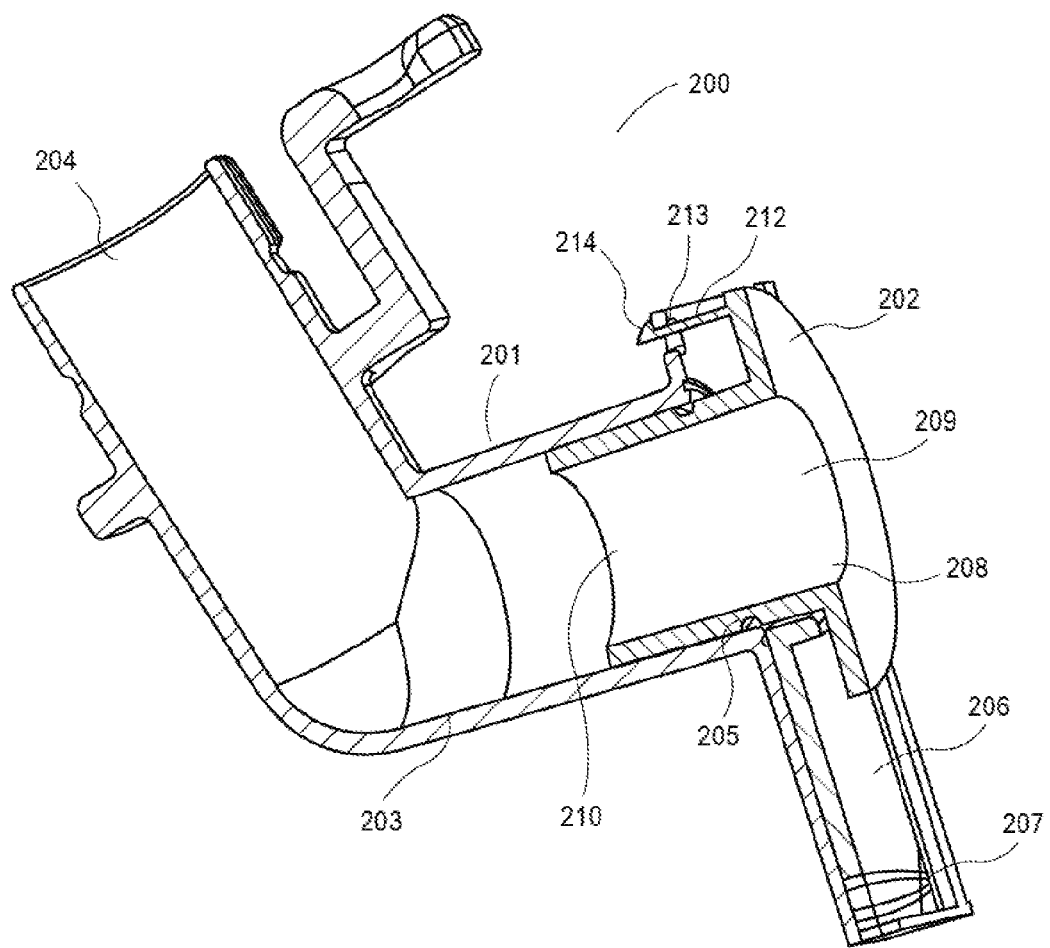
FIG. 7 illustrates a schematic cross-sectional view of the bag connector system of FIG. 4; in this particular figure, the coupling elements are coupled and the bag connector system is in the coupled state.
Figure 8:
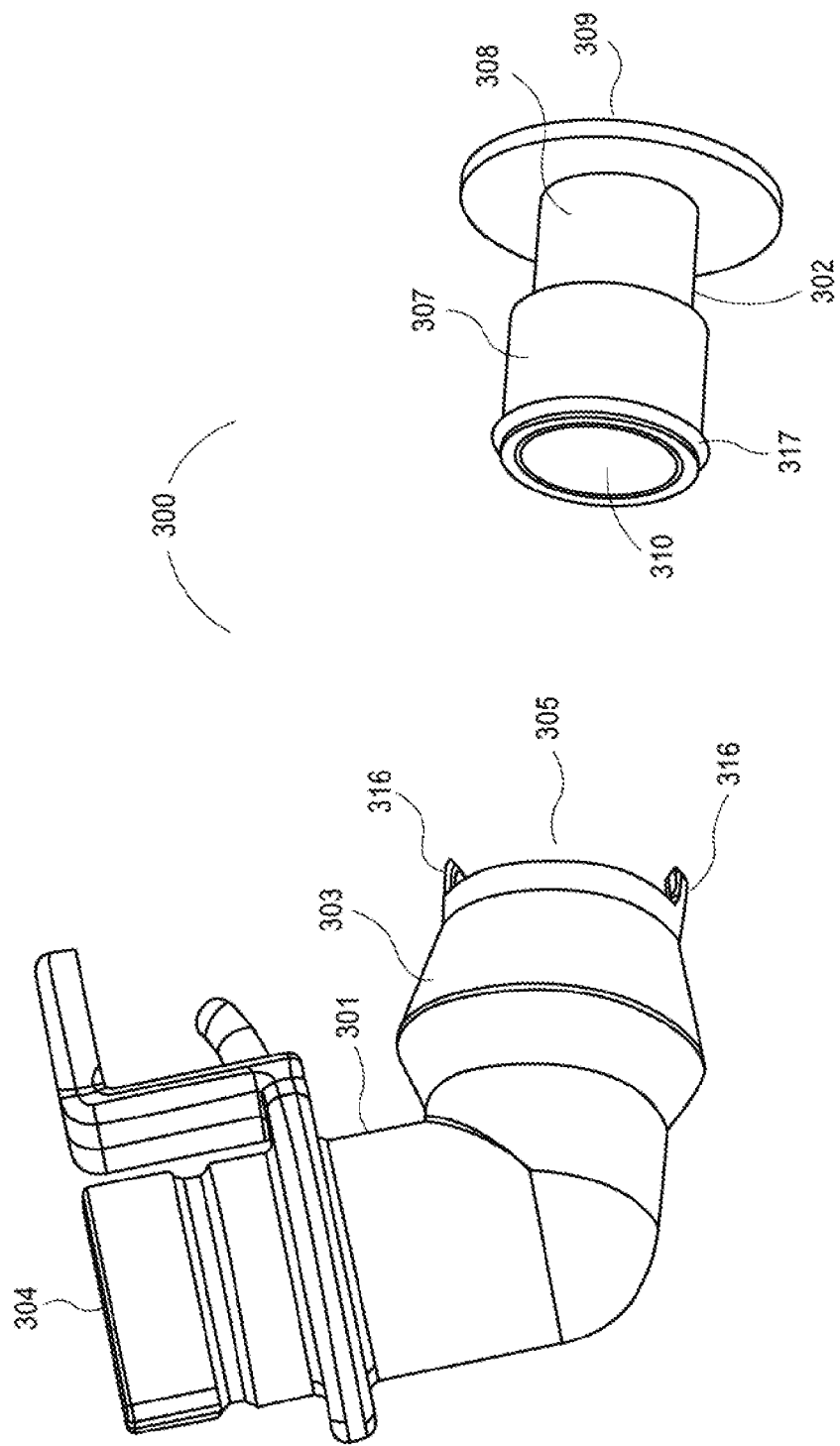
FIG. 8 illustrates a perspective view of a third embodiment of a bag connector system; in this particular figure, the coupling elements are aligned for coupling and the bag connector system is in the uncoupled state.
Figure 9A:
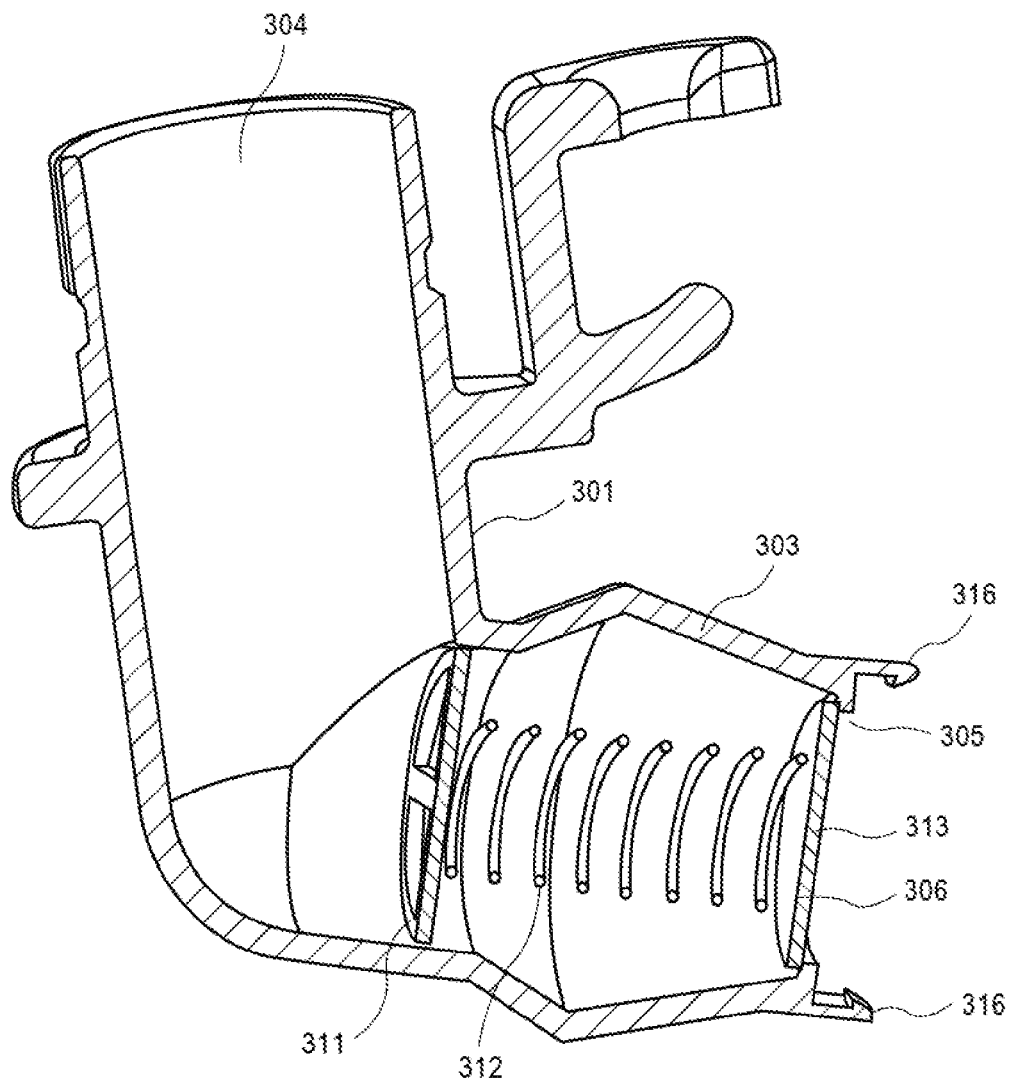
FIG. 9a illustrates a schematic cross-sectional view of the first coupling element the bag connector system of FIG. 8.
Figure 9B:
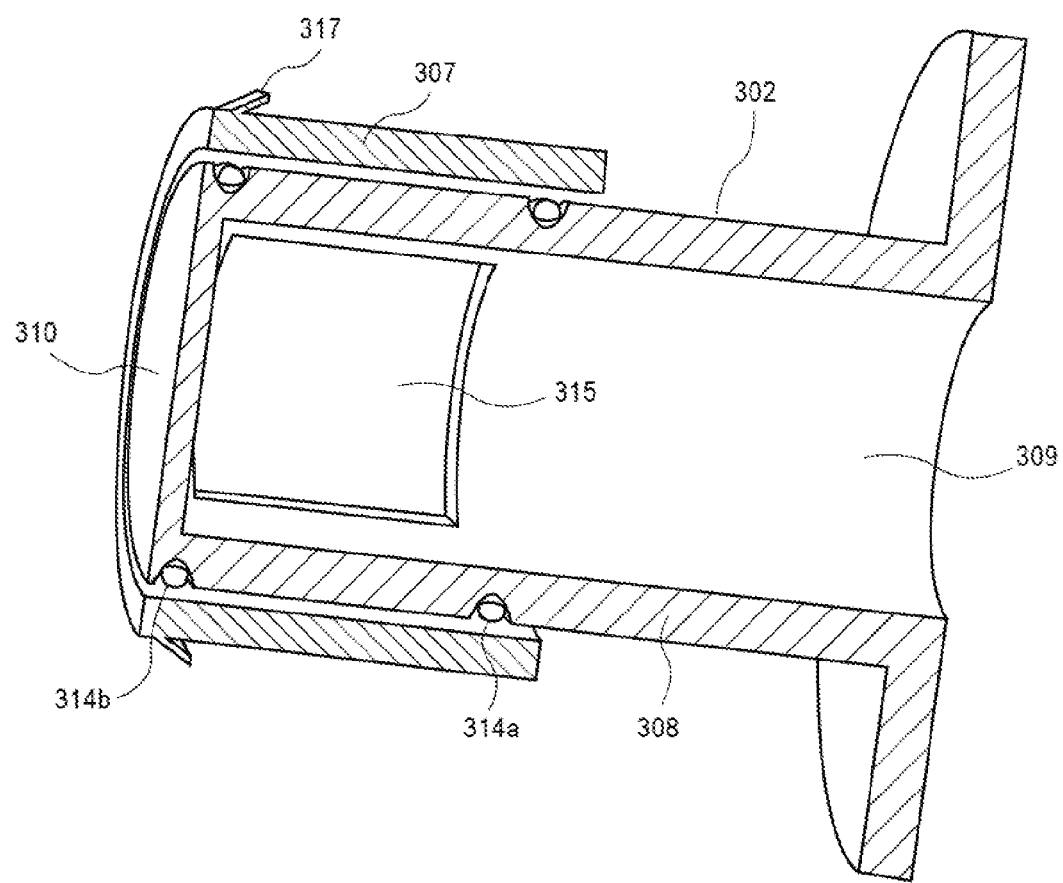
FIG. 9b illustrates a schematic cross-sectional view of the second coupling element of the bag connector system of FIG. 8.

Referring to FIG. 6, in the coupled state of the bag connector system 200, the sliding cover 206 is pushed towards the spring element 207 to expose the fluid outlet port 205 for coupling with the second coupling element 202. In this way, fluid within the housing 203 can flow through the coupled bag connector system 200 and be collected in a fluid storage container connected to the fluid outlet end 209 of the second coupling element 202.

The first coupling element 201 further comprises a washer 211, positioned just outside of the fluid outlet port 205, which interacts with the sliding cover 206 to create and maintain a seal with the sliding cover 206. The washer 211 may be made of silicone, fiber, rubber, or other elastomer.

The second coupling element 202 further comprises an O-ring 215, positioned around the outer surface of housing 208, which interacts with the inner surface of housing 203 at the fluid outlet port 205 to create and maintain a seal. The O-ring 215 may be made of silicone, rubber or other elastomer.

Each of the first coupling element 201 and the second coupling element 202 further comprises complementary components of a cantilever snap-fit mechanism, which can maintain the first coupling element and the second coupling element in a coupled state. In the coupled state of the bag connector system 200, a cantilever snap 212 located on the second coupling element 202 fits into a complementary slot 213 located on the sliding cover 206. The hook 214 prevents the cantilever snap 212 from being removed from slot 213, maintaining the coupling state of the first coupling element 201 and the second coupling element 202. One method to uncouple bag system 200 is to simultaneously depress hook 214 in a radial direction towards housing 203 and pull the coupling elements 201 and 202 apart.

Referring to FIGS. 8, 9a-b, 10, and 11, a third embodiment of a bag connector system 300 comprises a first coupling element 301 and a second coupling element 302. The first coupling element 301 comprises a housing 303 having a fluid inlet port 304 and a fluid outlet port 305. The second coupling element 302 comprises a housing 308 having a fluid outlet end 309 and a fluid inlet end 310. The fluid inlet end 310 has at least two openings 315 to allow fluid flow into the housing 308. A plurality of cantilever snaps 316 is located at the outer edge of fluid outlet port 305 and serves as a component of a snap-fit mechanism. Housing 303 and housing 308 may be made of plastic or any material suitable for containing and directing fluid.

The first coupling element 301 also comprises a spring loaded valve 306. The spring loaded valve 306 comprises of a spring seat 311, a spring element 312, and a flat cover 313. The spring seat 311, the spring element 312, and the flat cover 313 may all be integrated as one piece or manufactured separately and joined together to form the spring loaded valve 306. The spring seat 311 is perforated in a suitable manner so as to allow fluid flow through the spring seat 311. The spring seat 311 may be made of plastic or metal. The spring element 312 may be made of metal or plastic. The flat cover may be made of silicone, rubber, or other elastomer.

The second coupling element 302 also comprises a sliding cover 307 in the form of a movable hollow cylindrical member made of plastic that surrounds the fluid inlet end 310 of the housing 308. A ridge 317 is located on the outer surface of the sliding cover 307 and serves as a component of a snap-fit mechanism.

Figure 10:
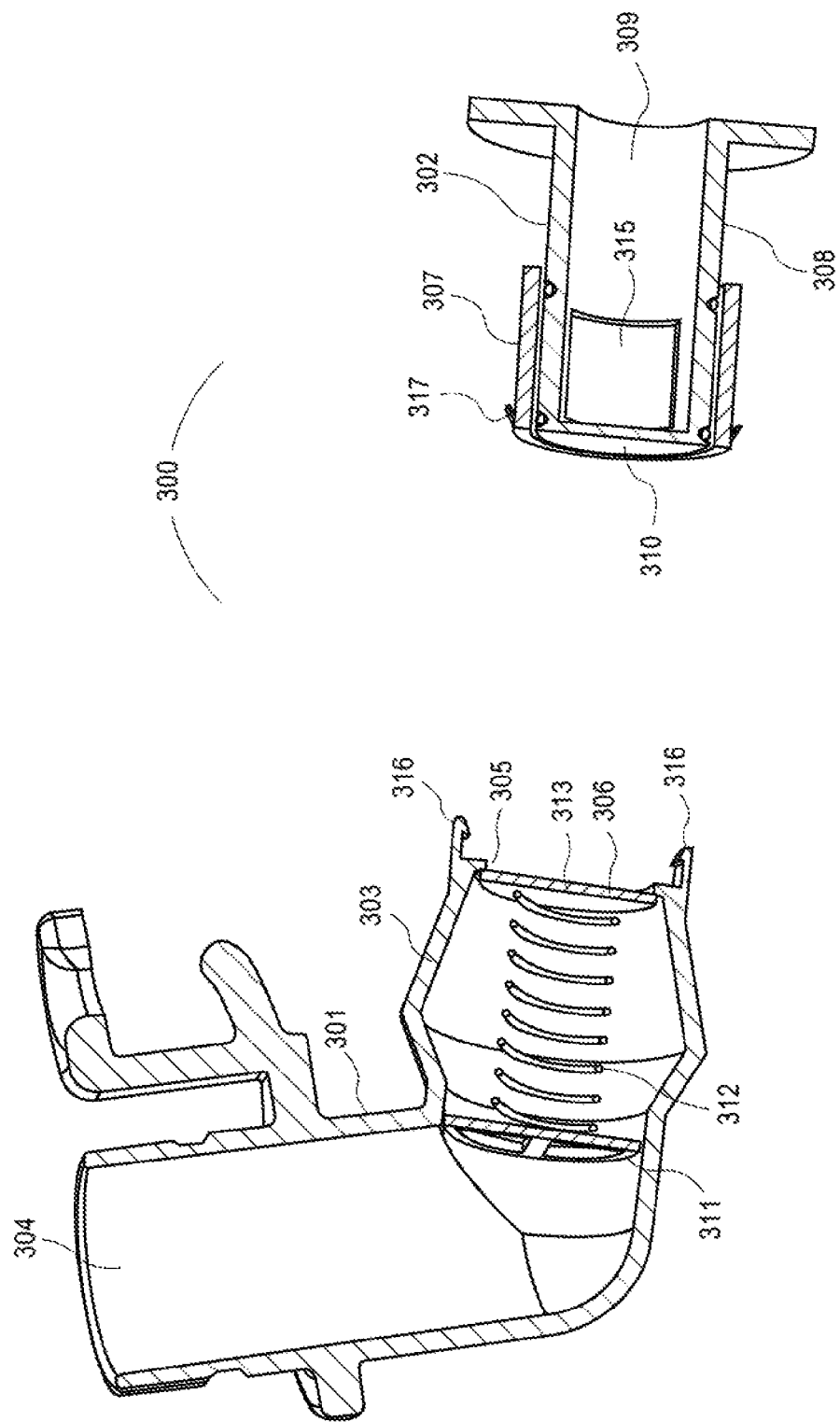
FIG. 10 illustrates a schematic cross-sectional view of the bag connector system of FIG. 8; in this particular figure, the coupling elements are aligned for coupling and the bag connector system is in the uncoupled state.

Referring to FIG. 10, in the uncoupled state of the bag connector system 300, the flat cover 313 of the spring loaded valve 306 is compressed against the inner wall of the fluid outlet port 305. The spring element 312 provides a slight compression, which creates and maintains a seal that prevents the exit of fluid through fluid outlet port 305. The sliding cover 307 surrounds the fluid inlet end 310 and completely covers the openings 315, creating a seal by interacting with O-rings 314a and 314b located on the outer surface of the fluid inlet port 310, at the distal and proximal ends of the openings 315. The O-rings 314a and 314b may be made of silicone, rubber, or other elastomer.

Figure 11:
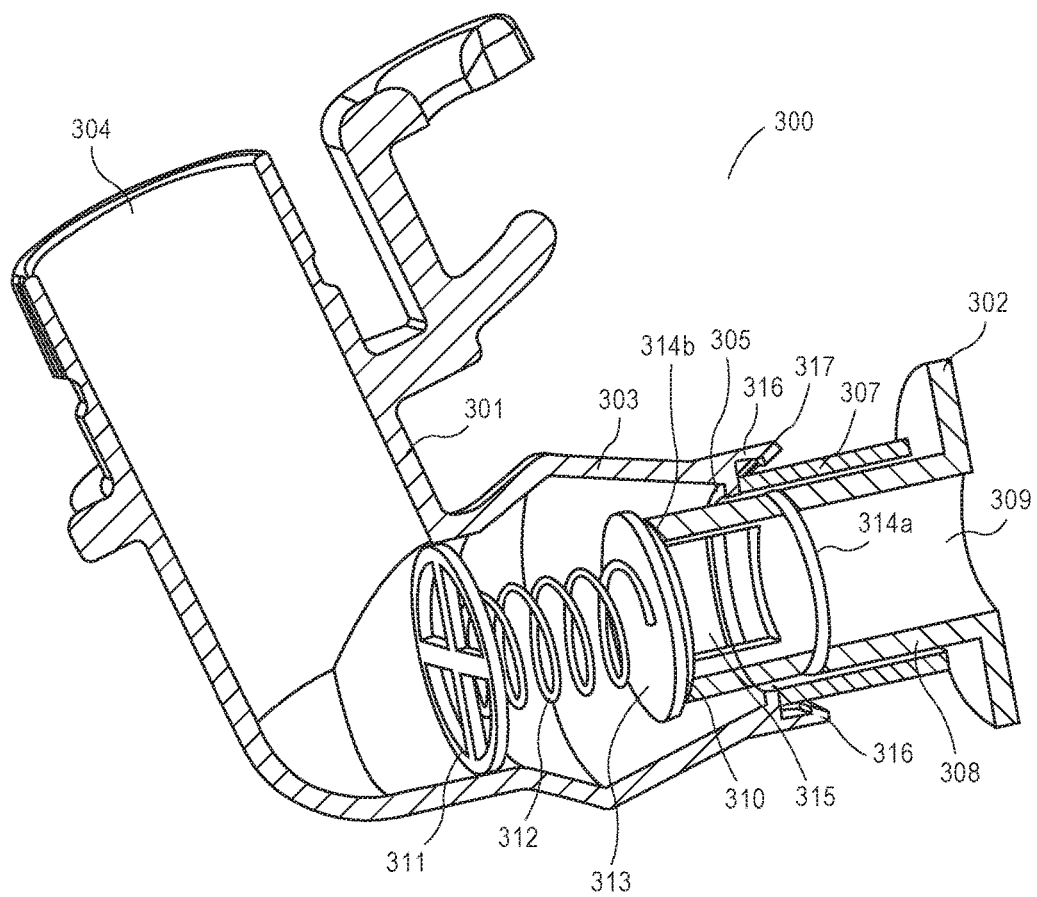
FIG. 11 illustrates a schematic cross-sectional view of the bag connector system of FIG. 8; in this particular figure, the coupling elements are coupled and the bag connector system is in the coupled state.

Referring to FIG. 11, in the coupled state of bag connector system 300, the flat cover 313 of the spring loaded valve 306 is pushed into the housing 303 by the fluid inlet end 310. Concomitantly, the sliding cover 307 is pushed by the outer edge of fluid outlet port 305 towards the fluid outlet end 309, providing complete or partial exposure of the openings 315 at the fluid inlet end 310. Fluid within the housing 303 can flow directly into fluid inlet end 310 through openings 315, as fluid inlet end 310 is positioned inside the housing 303. The plurality of cantilever snaps 316 on fluid outlet port 305 forms a snap-fit with the ridge 317 on the sliding cover 307. This snap-fit maintains the coupled state of the bag connector system 300.

To uncouple the first coupling element 301 and the second coupling element 302, sufficient pressure is applied by pulling the coupling elements 301 and 302 in opposing directions away from the snap-fit to cause one or more cantilever snaps 316 to lift away from the ridge 317, weakening the snap-fit until the snap-fit is released. Prior to the release of the snap-fit, the pulling motion moves the fluid inlet end 310 out of the housing 303, freeing the spring loaded valve 306 to seal the housing 303, and moves the sliding cover 307 to once again fully cover the openings 315 of the fluid inlet end 310.

Referring to FIGS. 12-15, a fourth embodiment of a bag connector system 400 comprises a first coupling element 401 and a second coupling element 402. The first coupling element 401 comprises a housing 403 having a fluid inlet port 404 and a fluid outlet port 405. The fluid outlet port 405 comprises a cap 406 and at least one opening 407 to allow fluid flow out of the housing 403. The second coupling element 402 comprises a housing 408 having a fluid inlet end 409 and a fluid outlet end 410. Housing 403 and housing 408 may be made of plastic or any material suitable for containing and directing fluid.

The first coupling element 401 also comprises a spring element 411 connected to a sliding cover 412 in the form of a movable hollow cylindrical member made of plastic or any other suitable material and comprises at least two external flanges 413a and 413b. In a modified embodiment (not shown), the sliding cover 412 has only one external flange 413. The spring element 411 and the sliding cover 412 can be joined to form a unitary object or two separate objects in direct contact with one another.

The second coupling element 402 also comprises a duckbill valve 414 and a valve holder 415. The duckbill valve 414 is made of silicone, rubber, or other elastomer. The valve holder 415 is made of plastic or any other suitable material. The duckbill valve 414 and the valve holder 415 can be an integrated piece or may comprise two separately manufactured pieces joined together. In other contemplated embodiments (not shown), the second coupling element 402 comprises a valve holder and a check valve selected from a ball check valve, a diaphragm check valve, a swing check valve, a stop-check valve, a lift-check valve, and an in-line check valve.

Figure 12:
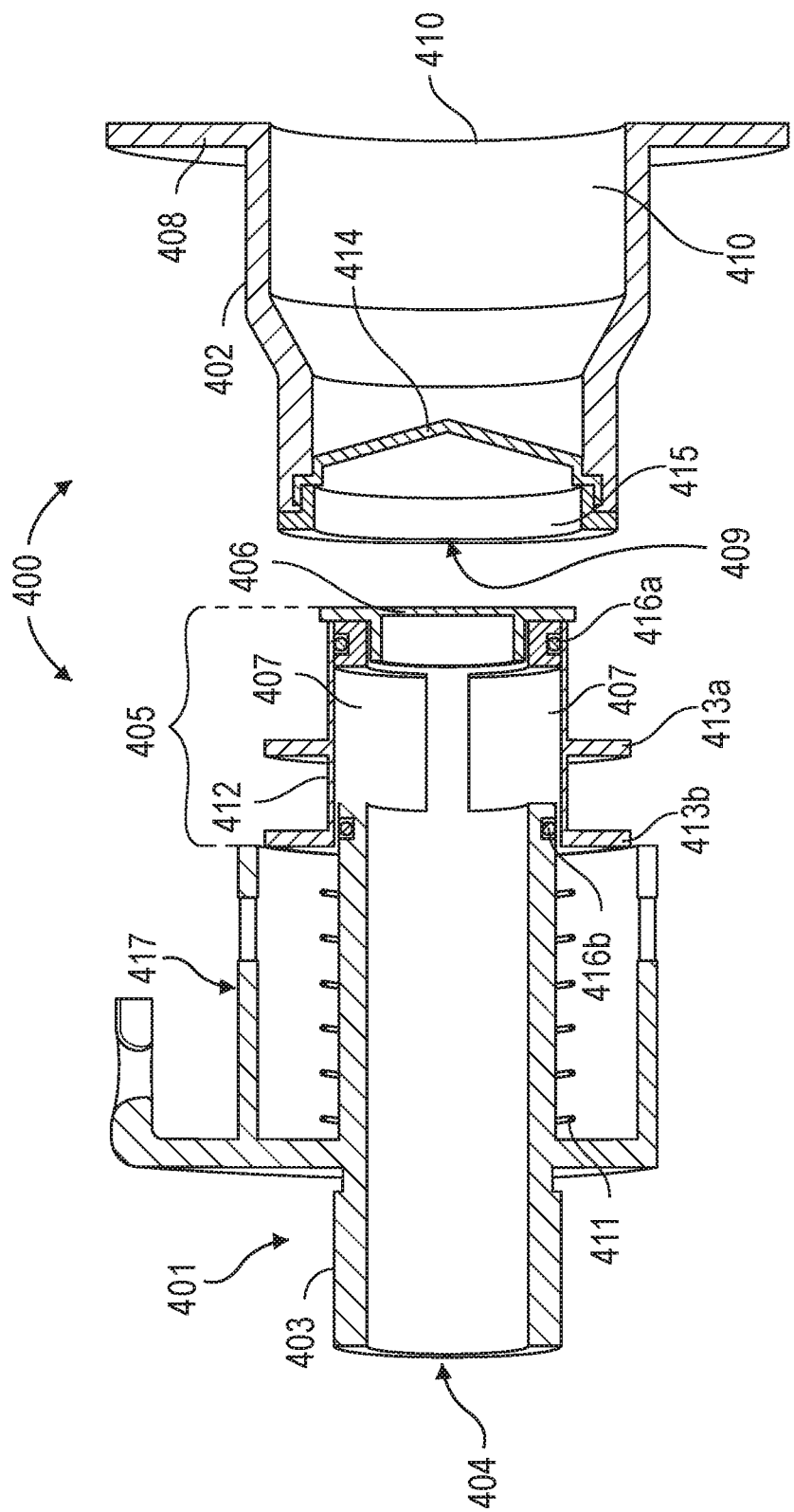
FIG. 12 illustrates a schematic cross-sectional view of a fourth embodiment of a bag connector system; in this particular figure, the coupling elements are aligned for coupling and the bag connector system is in the uncoupled state.
Figure 13:
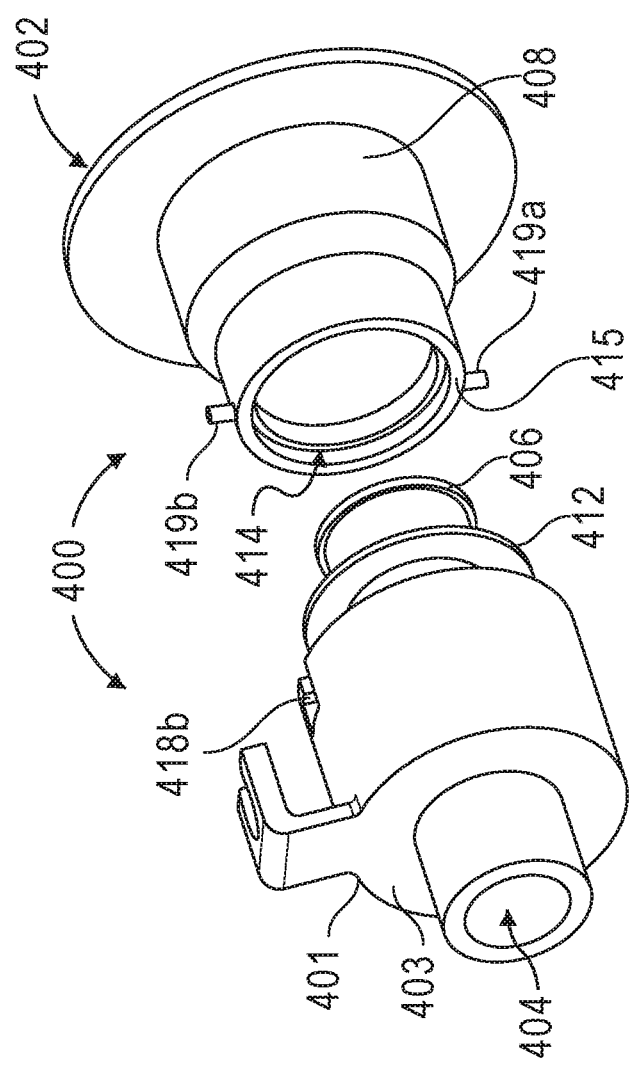
FIG. 13 illustrates a perspective view of the bag connector system of FIG. 12; in this particular figure, the coupling elements are aligned for coupling and the bag connector system is in the uncoupled state.
Figure 14:
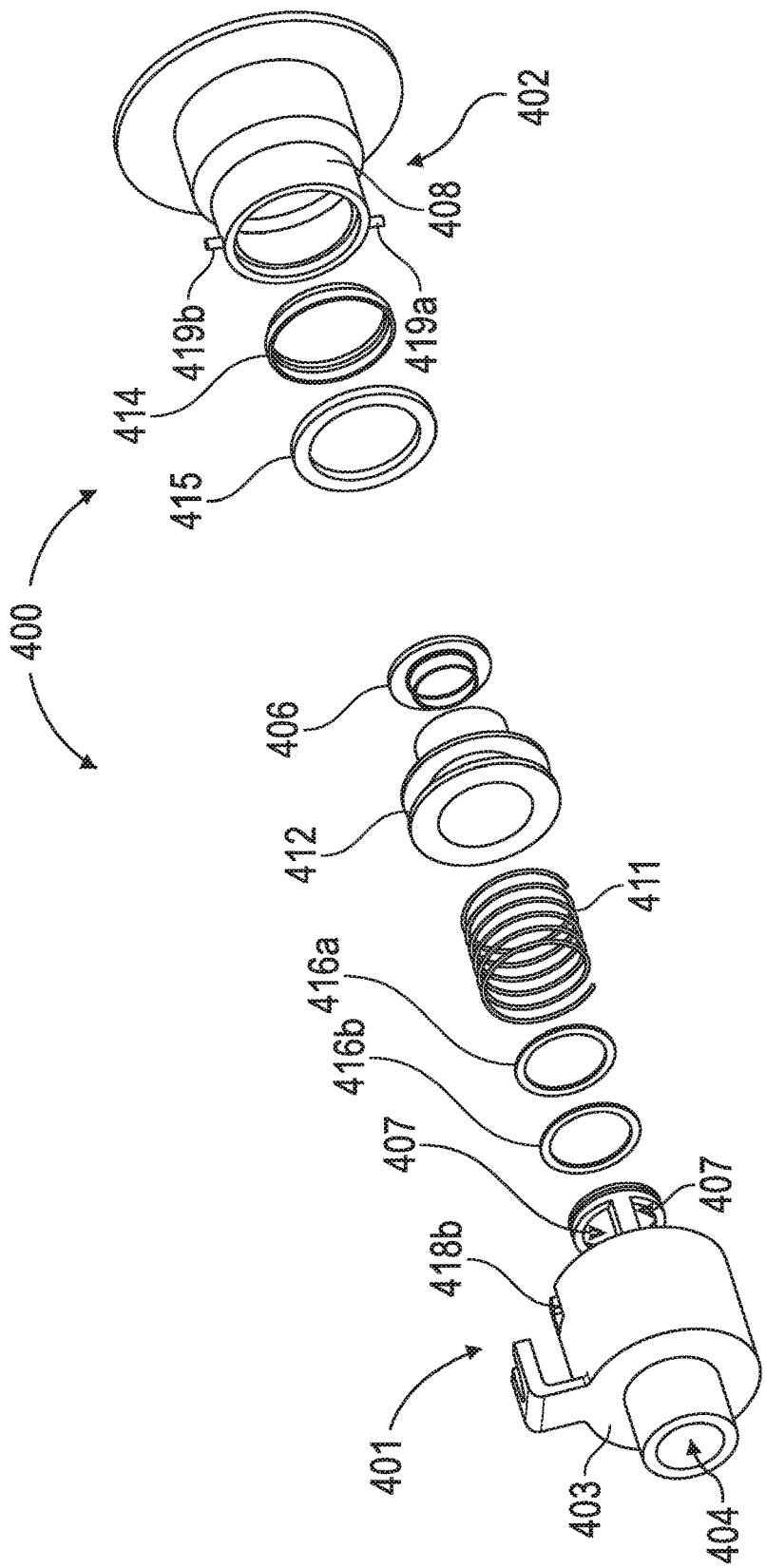
FIG. 14 illustrates an exploded view of the bag connector system of FIG. 12.

Referring to FIGS. 12 and 13, in the uncoupled state of the bag connector system 400, the sliding cover 412 completely covers the openings 407 of the housing 403, creating a seal by interacting with O-rings 416a and 416b located on housing 403 at the distal and proximal ends of the openings 407. The O-rings 416a and 416b may be made of silicone, rubber, or other elastomer. The duckbill valve 414 is in the closed position, preventing backflow of fluid from housing 408.

Figure 15:
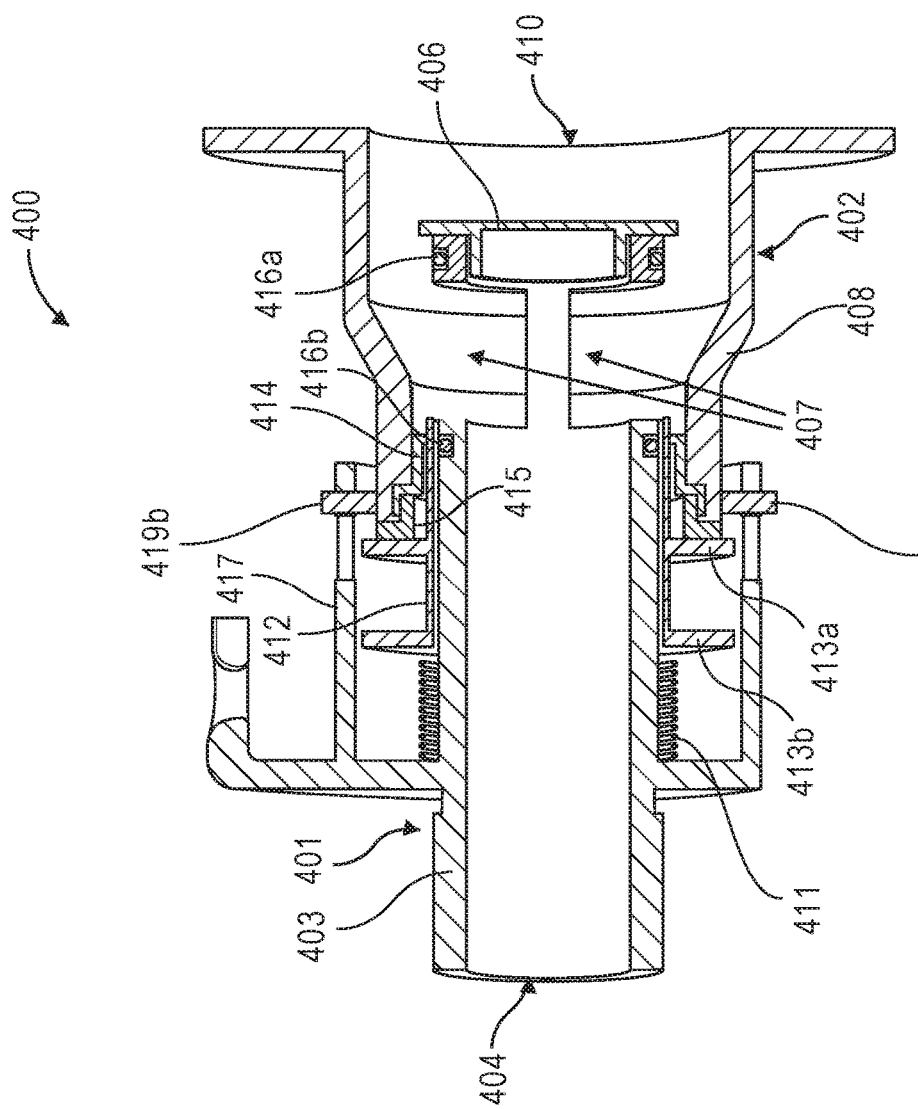
FIG. 15 illustrates a schematic cross-sectional view of the bag connector system of FIG. 12; in this particular figure, the coupling elements are coupled and the bag connector system is in the coupled state.

Referring to FIG. 15, in the coupled state of the bag connector system 400, the valve holder 415 is pushed against the flange 413a of the sliding cover 412, until the flange 413b compresses the spring element 411 and the valve holder 415 has entered the fluid outlet port 405. In a modified embodiment, the valve holder 415 is pushed against the flange 416 of the sliding cover 412, until the flange 413b also compresses the spring element 411.

The movement of the sliding cover 412 provides partial or complete exposure of the openings 407. Concomitantly, the cap 406 is pushed against the duckbill valve 414, partially or fully opening this valve and situating the partial or completely exposed openings 407 to be within the housing 408. Fluid within the housing 403 can now flow directly through openings 407 and into housing 408.

Each of the first coupling element 401 and the second coupling element 402 further comprises complementary components of a locking mechanism, which maintains the first coupling element and the second coupling element in a coupled state. Such locking mechanisms include a twist lock-in mechanism, bayonet latch, or other locking mechanism which maintains a coupled state between the first coupling element and the second coupling element. For example, in one embodiment, the first coupling element 401 comprises at least one of the complementary components of a locking mechanism. The external edge of the fluid outlet port 405 is a rotatable locking member 417 having two slots 418a and 418b which receive pins 419a and 419b located on the outer surface of the fluid inlet end 409. When the twist lock-in mechanism is in a first position, the pins 419a and 419b can pass through the complementary slots 418a and 418b, easily coupling or uncoupling the first coupling element 401 and the second coupling element 402. When the twist lock-in mechanism is in a second position, the pins 419a and 419b cannot pass through the complementary slots 418a and 418b, maintaining the first coupling element 401 and the second coupling element 402 in a coupled state. The twist lock-in mechanism is toggled between the first and second positions by rotating the coupled coupling elements in opposing directions along the axis of the fluid flow pathway.

To uncouple the first coupling element 401 and the second coupling element 402, the twist lock-in mechanism is toggled to the first position and the two coupling elements 401 and 402 are pulled in opposing directions away from each other. The spring element 411 pushes the sliding cover 412 to once again fully cover the openings 407. The duckbill valve 414 also self-seals upon uncoupling of the first coupling element 401 and the second coupling element 402.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A bag connector system comprising:
   a) a first coupling element comprising a first housing having a first fluid inlet and a first fluid outlet, the first coupling element further comprising an O-ring and a self-closing seal to prevent fluid flow from exiting the first fluid outlet of the first coupling element, wherein the self-closing seal comprises a sliding cover or a spring loaded valve; and
   b) a second coupling element comprising a second housing having a second fluid inlet and a second fluid outlet, and a check valve disposed in or around the second housing, the second coupling element configured to displace the self-closing seal of the first coupling element to allow fluid flow between the first coupling element and the second coupling element, wherein the check valve is selected from a duckbill valve, diaphragm check valve, swing check valve, stop-check valve, lift-check valve, in-line check valve, and leaf valve, and the check valve is pushed by the first fluid outlet of the first coupling element towards the second fluid outlet of the second coupling element during coupling of the first coupling element and the second coupling element, thereby providing complete or partial exposure of an opening at the first fluid outlet of the first coupling element.

2. The bag connector system of claim 1, wherein each of the first coupling element and the second coupling element further comprises a means to maintain the first coupling element and the second coupling element in a coupled state.

3. The bag connector system of claim 1, wherein the self-closing seal is positioned within the housing of the first coupling element.

4. The bag connector system of claim 1, wherein the self-closing seal is positioned outside of the housing of the first coupling element.

5. The bag connector system of claim 1, wherein the self-closing seal comprises a flapper connected to a leaf spring.

6. The bag connector system of claim 5, wherein the housing of the first coupling element further comprises a washer.

7. The bag connector system of claim 5, wherein each of the first coupling element and the second coupling element further comprises a means to maintain the first coupling element and the second coupling element in a coupled state.

8. The bag connector system of claim 7, wherein the means to maintain the first coupling element and the second coupling element in a coupled state comprises a twist lock-in mechanism.

9. The bag connector system of claim 1, wherein the housing of the first coupling element further comprises a washer.

10. The bag connector system of claim 2, wherein the means to maintain the first coupling element and the second coupling element in a coupled state comprises a single cantilever snap-fit mechanism.

11. The bag connector system of claim 2, wherein the second coupling element further comprises an O-ring positioned on the outer surface of the housing.

12. The bag connector system of claim 1, wherein the spring-loaded valve comprises a spring seat, a spring element, and a flat cover.

13. The bag connector system of claim 1, wherein the second coupling element further comprises a sliding cover positioned over the second fluid inlet.

14. The bag connector system of claim 2, wherein the means to maintain the first coupling element and the second coupling element in a coupled state comprises a plurality of cantilever snaps at the first fluid outlet of the first coupling element which forms a snap-fit with the sliding cover on the first coupling element.

15. The bag connector system of claim 2, wherein the means to maintain the first coupling element and the second coupling element in a coupled state comprises a twist lock-in mechanism.

16. The bag connector system of claim 1, wherein the spring-loaded valve is compressed into the first housing by the second fluid inlet of the second coupling element during coupling of the first coupling element and the second coupling element.

17. The bag connector system of claim 2, wherein the second coupling element comprises a ridge which forms a snap-fit with a cantilever snap of the first coupling element to maintain the first coupling element and the second coupling element in the coupled state.

18. The bag connector system of claim 1, wherein the second fluid inlet of the second coupling element comprises an opening, and in an uncoupled state of the bag connector system, the check valve covers the opening; wherein during coupling of the first coupling element and the second coupling element, the check valve is pushed towards the second fluid outlet of the second coupling element to expose the opening.

19. A medical appliance comprising a fluid storage container and a bag connector system, the bag connector system comprising:
   a) a first coupling element comprising a first housing having a first fluid inlet and a first fluid outlet, the first coupling element further comprising an O-ring and a self-closing seal to prevent fluid flow from exiting the first fluid outlet of the first coupling element, wherein the self-closing seal comprises a sliding cover or a spring-loaded valve; and
   b) a second coupling element comprising a second housing having a second fluid inlet and a second fluid outlet, and a check valve disposed in or around the second housing, the second coupling element configured to displace the self-closing seal of the first coupling element to allow fluid flow between the first coupling element and the second coupling element, wherein the check valve is selected from a duckbill valve, diaphragm check valve, swing check valve, stop-check valve, lift-check valve, in-line check valve, and leaf valve; and the check valve is pushed by the first fluid outlet of the first coupling element towards the second fluid outlet of the second coupling element during coupling of the first coupling element and the second coupling element, thereby providing complete or partial exposure of an opening at the first fluid outlet of the first coupling element; and
  wherein the second fluid outlet of the second coupling element is connected to the fluid storage container.

20. The medical appliance of claim 19, wherein the self-closing seal is a flapper connected to a leaf spring, a sliding cover connected to a spring element, or a spring-loaded valve.

21. The medical appliance of claim 19, wherein each of the first coupling element and the second coupling element further comprises a means to maintain the first coupling element and the second coupling element in a coupled state.

22. The medical appliance of claim 21, wherein the means to maintain the first coupling element and the second coupling element in a coupled state is selected from:
   a) a twist lock-in mechanism;
   b) a single cantilever snap-fit mechanism; and
   c) a multiple cantilever snap-fit mechanism comprising a plurality of cantilever snaps at the first fluid outlet of the first coupling element which forms a snap-fit with the sliding cover on the first coupling element.

\* \* \* \* \*